(12) United States Patent
Tsujikawa et al.

(10) Patent No.: US 9,212,169 B2
(45) Date of Patent: Dec. 15, 2015

(54) BENZIMIDAZOLE DERIVATIVE AND USE THEREOF

(71) Applicants: HYOGO COLLEGE OF MEDICINE, Nishinomiya-shi, Hyogo (JP); KAGOSHIMA UNIVERSITY, Kagoshima-shi, Kagoshima (JP); OSAKA UNIVERSITY, Suita-shi, Osaka (JP)

(72) Inventors: Kazutake Tsujikawa, Suita (JP); Akito Tanaka, Kobe (JP); Shunji Aoki, Kobe (JP); Hiroaki Mizuno, Kobe (JP); Miyuki Tokoro, Kobe (JP); Tatsuhiko Furukawa, Kagoshima (JP)

(73) Assignees: HYOGO COLLEGE OF MEDICINE, Nishinomiya (JP); KAGOSHIMA UNIVERSITY, Kagoshima (JP); OSAKA UNIVERSITY, Suita (JP)

( * ) Notice: Subject to any disclaimer, the term of this patent is extended or adjusted under 35 U.S.C. 154(b) by 0 days.

(21) Appl. No.: 14/382,048

(22) PCT Filed: Mar. 1, 2013

(86) PCT No.: PCT/JP2013/055752
§ 371 (c)(1),
(2) Date: Aug. 29, 2014

(87) PCT Pub. No.: WO2013/129674
PCT Pub. Date: Sep. 6, 2013

(65) Prior Publication Data
US 2015/0011600 A1 Jan. 8, 2015

(30) Foreign Application Priority Data

Mar. 1, 2012 (JP) .................................. 2012-045267

(51) Int. Cl.
C07D 403/04 (2006.01)

(52) U.S. Cl.
CPC .................................. C07D 403/04 (2013.01)

(58) Field of Classification Search
USPC ..................................................... 548/306.1
See application file for complete search history.

(56) References Cited

U.S. PATENT DOCUMENTS

| | | | |
|---|---|---|---|
| 2,895,955 | A | 7/1959 | Heseltine |
| 4,189,321 | A | 2/1980 | Kojima et al. |
| 2009/0130662 | A1 | 5/2009 | Tsujikawa et al. |
| 2010/0297145 | A1 | 11/2010 | Tsujikawa et al. |
| 2011/0237907 | A1 | 9/2011 | Kirsch et al. |
| 2012/0196883 | A1 | 8/2012 | Surmeier, Jr. et al. |
| 2012/0232110 | A1 | 9/2012 | Moy et al. |

FOREIGN PATENT DOCUMENTS

| | | |
|---|---|---|
| GB | 813866 | 5/1959 |
| JP | 54-048540 A | 4/1979 |
| JP | 64-000541 A | 1/1989 |
| JP | 2011-001286 A | 1/2011 |
| WO | WO 2006/098464 A1 | 9/2006 |
| WO | WO 2007/015587 A1 | 2/2007 |
| WO | WO 2010/059241 A2 | 5/2010 |
| WO | WO 2010/151784 A2 | 12/2010 |
| WO | WO 2011/022721 A1 | 2/2011 |

OTHER PUBLICATIONS

Chemical Abstracts Registry No. 891457-33-3, indexed in the Registry file on STN CAS Online Jul. 10, 2006.*
Chemical Abstracts Registry No. 944780-04-5, indexed in the Registry file on STN CAS Online Aug. 16, 2007.*
Chemical Abstracts Registry No. 1006582-11-1, indexed in the Registry file on STN CAS Online Mar. 4, 2008.*
Chemical Abstracts Registry No. 925563-88-8, indexed in the Registry file on STN CAS Online Mar. 8, 2007.*
Chemical Abstracts Registry No. 944780-06-7, indexed in the Registry file on STN CAS Online Aug. 16, 2007.*
Chemical Abstracts Registry No. 944780-05-6, indexed in the Registry file on STN CAS Online Aug. 16, 2007.*
Cadieux et al., *Bioorganic & Medicinal Chemistry Letters*, 22(1): 90-95 (2012).
Garnovskii et al., *Khimiya Geterotsiklicheskikh Soedinenii*, 5: 610-613 (1970).
Geiss et al., *Journal of Bimolecular Screening*, 16(8): 852-861 (2011).
Konishi et al., *Clin. Cancer Res*, 11(14): 5090-5097 (2005).
LeCount et al., *Journal of the Chemical Society, Perkin Transactions 1: Organic and Bio-Organic Chemistry* [1972-1999], 2: 297-301 (1974).
Sharma et al., *Indian Journal of Heterocyclic Chemistry*, 14(2): 161-162 (Oct.-Dec. 2004).
STN International, "3H-Pyrazol-3-one, 2-(1H-benzimidazol-2-yl)-2,4-dihydro-5-methyl-4-[[(4-methylphenyl)amino]methylene]-, (4E)-," CAS Registry No. 1164464-71-4 (Jul. 19, 2009).
STN International, "3H-Pyrazol-3-one, 2-(1H-benzimidazol-2-yl)-4-[[(4-ethoxyphenyl)amino]methylene]-2,4-dihydro-5-methyl-, (4Z)-," CAS Registry No. 1164484-95-0 (Jul. 19, 2009).
Tasaki et al., *British Journal of Cancer*, 104(4): 700-706 (2011).
Tosun et al., *Journal of Faculty of Pharmacy Gazi University*, 12(2): 145-152 (1995).
Tsujikawa et al., *The 123rd Annual Meeting of Pharmaceutical Society of Japan, Abstracts*, 4: 15, Abstract 29[P2] I-521 (2003).
Zhu et al., *Cancer Research*, 70(20): 9772-8002 (2010).
Japanese Patent Office, International Search Report in International Patent Application No. PCT/JP2013/055752 (May 28, 2013).

* cited by examiner

Primary Examiner — Laura L. Stockton
(74) Attorney, Agent, or Firm — Leydig, Voit & Mayer, Ltd.

(57) ABSTRACT

The present invention aims to provide a compound capable of inhibiting PCA-1 that can be a target for a novel treatment method of various diseases, and pharmaceutical use of the compound. A compound represented by the formula (I):

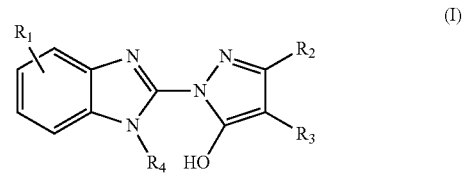

wherein each symbol is as defined in the DESCRIPTION, or a pharmaceutically acceptable salt thereof.

4 Claims, 1 Drawing Sheet

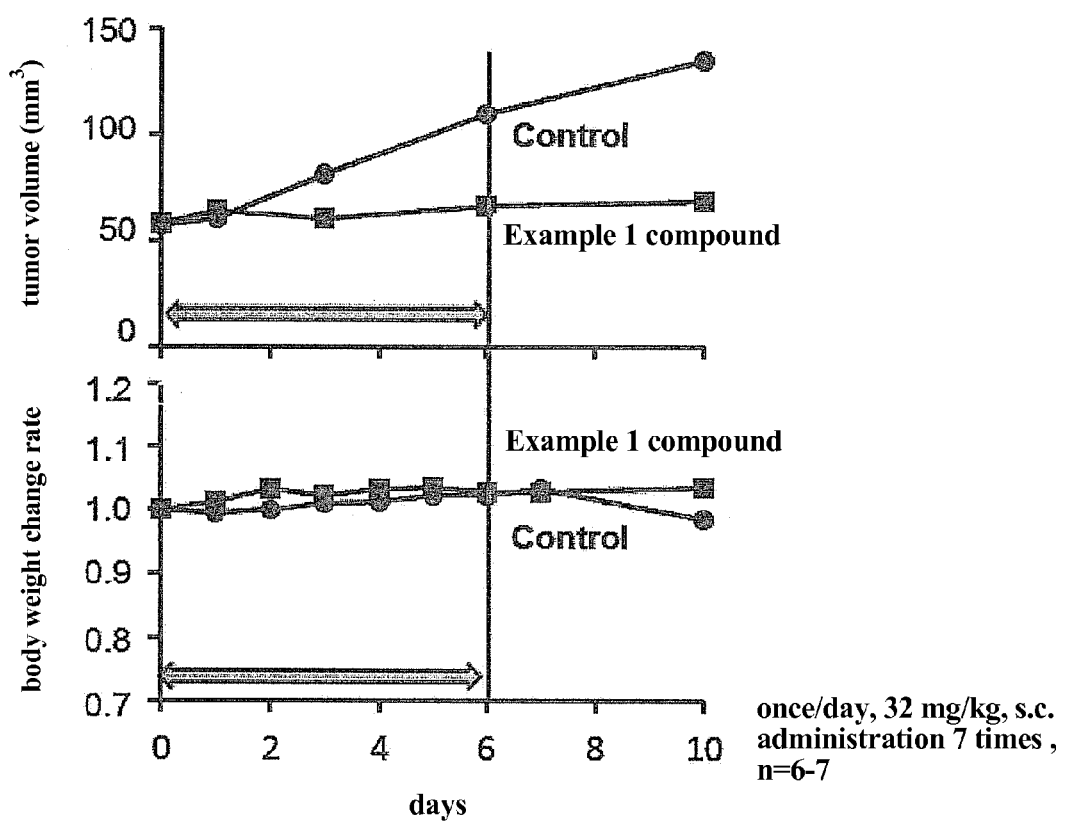

BENZIMIDAZOLE DERIVATIVE AND USE THEREOF

CROSS-REFERENCE TO RELATED APPLICATIONS

This patent application is the U.S. national phase of International Patent Application No. PCT/JP2013/055752, filed Mar. 1, 2013, which claims the benefit of Japanese Patent Application No. 2012-045267, filed Mar. 1, 2012.

TECHNICAL FIELD

The present invention relates to a novel benzimidazole derivative and use thereof. More particularly, the present invention relates to a novel benzimidazole derivative having a Prostate Cancer Antigen-1 (PCA-1) inhibitory activity and a PCA-1 inhibitor, a medicament and the like containing the compound.

BACKGROUND ART

Prostate cancer, which occupies the number one in the morbidity rate and mortality in Europe and the United States, also shows a rapid increase in the morbidity rate also in Japan due to the westernization of the eating habits. The early-stage cancer of prostate cancer can be completely cured by operative treatment and the like, and elderly citizens with prostate cancer or progressive cancer, for whom an operative treatment is difficult, undergo a hormone therapy. During such treatment, however, hormone therapy resistant prostate cancer emerges, and therefore, an effective treatment method of prostate cancer has not been currently established as the situation stands.

On the other hand, pancreatic cancer is held to be one of the cancers most difficult to treat at present. In pancreatic cancer, even when the tumor is removed by surgery, about 90% of them have a relapse and die. For topical progressive irremovable pancreatic cancer, multiple drug combination therapy mainly using gemcitabine hydrochloride and 5-FU and the like are applied, and when distant metastasis is found, a multiple drug combination therapy mainly using gemcitabine hydrochloride, and the like are applied. Nevertheless, the prognosis is 4-6 months in a median value.

Lung cancer is the top in the number of those died of cancer in Japan. Particularly, the number of patients of non-small cell lung cancer is the highest in the lung cancer. As a therapeutic drug therefor, chemotherapeutic agents such as taxane group and the like have been used; however, only about 30% regression is observed. As a molecular target drug, gefitinib is applicable to patients having mutated EGFR Therefore, the development of an effective therapeutic drug for these types of cancer is desired, and the foundation for drug discovery needs to be established early.

A novel gene (Prostate Cancer Antigen-1: PCA-1) has been reported, which highly expresses in prostate cancer, and does not show high expression in normal prostate epithelial cell and benign prostatic hyperplasia which is a benign tumor (non-patent document 1, non-patent document 2). There have been reported a method using the expression state of PCA-1 for the diagnosis of prostate cancer (patent document 1), and an apoptosis promoter, a cell proliferation inhibitor, an agent for the prophylaxis or treatment of cancer and the like, which contain, as an active ingredient, a compound that suppresses the expression or function of PCA-1 (patent document 2). PCA-1 is also highly expressed in pancreatic cancer (patent document 3) and non-small cell lung cancer (non-patent document 3). When the PCA-1 expression in these cancer cells was suppressed using siRNA, a remarkable suppressive action on the growth of prostate cancer cell (patent document 2), pancreatic cancer cell (patent document 3), and non-small cell lung cancer was observed (non-patent document 3). In addition, a tumor formed by transplanting cancer cells to a mouse showed regression by the administration of siRNA to PCA-1. These results suggest that PCA-1 can be a new molecular target in the cancer treatment for prostate cancer, pancreatic cancer and the like.

Moreover, since tRNA demethylated by PCA-1 increases the protein translation efficiency, PCA-1 is also useful for the diseases (e.g., brain neurodegenerative disease, arteriosclerosis) possibly caused by an abnormal protein.

On the other hand, a benzimidazole derivative having the following structure has been reported (patent documents 4, 5); however, its action on the enzyme activity of PCA-1 is not known.

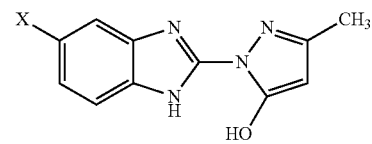

X = Me (patent document 4)
X = Cl, EtO (patent document 5)

DOCUMENT LIST

Patent Documents patent document 1: WO2006/098464
patent document 2: WO2007/015587
patent document 3: JP-A-2011-1286
patent document 4: U.S. Pat. No. 2,895,955
patent document 5: GB-B-813866

Non-Patent Documents non-patent document 1: The 123rd Annual Meeting of the Pharmaceutical society of Japan, Abstracts 4, p. 15, 2003
non-patent document 2: Konishi N et al., Clin Cancer Res. 2005 Jul. 15; 11(14): 5090-7.
non-patent document 3: Tasaki M et al., Br J Cancer. 2011 104(4): 700-6.

SUMMARY OF THE INVENTION

Problems to be Solved by the Invention

The present invention aims to provide a compound effective for a cancer for which an effective treatment method has not been established and/or which shows poor prognosis, such as cancer, particularly prostate cancer, pancreatic cancer and non-small cell lung cancer, and an anti-cancer agent and the like containing said compound as an active ingredient. Furthermore, the present invention aims to provide a compound capable of inhibiting PCA-1, which can be a target for a novel treatment method for various diseases, and pharmaceutical use of said compound.

Means of Solving the Problems

The present inventors have conducted intensive studies in view of the above-mentioned problem. To be specific, they took note of PCA-1 suggested to be a new molecular target in the cancer treatment of, for example, prostate cancer, pancreatic cancer and the like. Using a screening system that measures the enzyme activity that demethylates methylated cytosine possessed by PCA-1, they have searched for a substance that inhibits the enzyme activity. As a result, they have obtained a compound that inhibits the enzyme activity of PCA-1, and further suppresses the growth of prostate cancer cells and pancreatic cancer cells in vitro. Using the compound as a seed compound, they have conducted further studies of the structure-activity correlation and succeeded in the creation of a series of advantageous compounds, which resulted in the completion of the present invention.

Accordingly, the present invention provides the following.

[1] A compound represented by the formula (I):

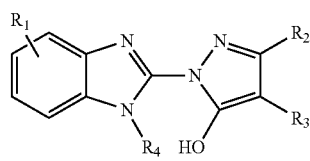

(I)

wherein $R_1$ is a hydrogen atom or a substituent; $R_2$ is a substituent; $R_3$ is a hydrogen atom or a substituent; and $R_4$ is a hydrogen atom or a substituent;
provided that when $R_1$ is a hydrogen atom, then $R_3$ is not methyl; and when $R_1$ is a substituent, then $R_3$ is not a hydrogen atom,
or a pharmaceutically acceptable salt thereof.

[2] The compound of the above-mentioned [1], wherein $R_1$ is a hydrogen atom;
an optionally substituted $C_{1-6}$ alkyl group;
an optionally substituted $C_{6-10}$ aryl group; or
a halogen atom,
or a pharmaceutically acceptable salt thereof.

[3] The compound of the above-mentioned [1], wherein $R_1$ is a hydrogen atom;
a $C_{1-6}$ alkyl group optionally substituted by a halogen atom;
a $C_{6-10}$ aryl group optionally substituted by one or more substituents selected from the group consisting of a halogen atom and a $C_{1-6}$ alkyl group; or
a halogen atom,
or a pharmaceutically acceptable salt thereof.

[4] The compound of the above-mentioned [1], wherein $R_2$ is an optionally substituted $C_{1-6}$ alkyl group; or
an optionally substituted $C_{6-10}$ aryl group,
or a pharmaceutically acceptable salt thereof.

[5] The compound of the above-mentioned [1], wherein $R_2$ is a $C_{1-6}$ alkyl group or a $C_{6-10}$ aryl group,
or a pharmaceutically acceptable salt thereof.

[6] The compound of the above-mentioned [1], wherein $R_3$ is a hydrogen atom;
an optionally substituted $C_{7-11}$ aralkyl group;
an optionally substituted $C_{6-10}$ aryl group; or
an optionally substituted $C_{1-6}$ alkyl group,
or a pharmaceutically acceptable salt thereof.

[7] The compound of the above-mentioned [1], wherein $R_3$ is a hydrogen atom;
a $C_{7-11}$ aralkyl group optionally substituted by one or more substituents selected from the group consisting of a halogen atom, a $C_{1-6}$ alkyl group optionally substituted by a halogen atom, a $C_{6-10}$ aryl group and a $C_{1-6}$ alkoxy group;
a $C_{6-10}$ aryl group; or
a $C_{1-6}$ alkyl group optionally substituted by one or more substituents selected from the group consisting of a $C_{6-10}$ aryl group, a $C_{1-6}$ alkoxy-carbonyl group, a carboxyl group and a $C_{3-6}$ cycloalkyl group,
or a pharmaceutically acceptable salt thereof.

[8] The compound of the above-mentioned [1], wherein $R_4$ is a hydrogen atom; or
an optionally substituted $C_{1-6}$ alkyl group,
or a pharmaceutically acceptable salt thereof.

[9] The compound of the above-mentioned [1], wherein $R_4$ is a hydrogen atom, or a pharmaceutically acceptable salt thereof.

[10] The compound of the above-mentioned [1], wherein $R_1$ is
a hydrogen atom;
a $C_{1-6}$ alkyl group optionally substituted by a halogen atom;
a $C_{6-10}$ aryl group optionally substituted by one or more substituents selected from the group consisting of a halogen atom and a $C_{1-6}$ alkyl group; or
a halogen atom,
$R_2$ is
a $C_{1-6}$ alkyl group or a $C_{6-10}$ aryl group,
$R_3$ is
a hydrogen atom;
a $C_{7-11}$ aralkyl group optionally substituted by one or more substituents selected from the group consisting of a halogen atom, a $C_{1-6}$ alkyl group optionally substituted by a halogen atom, a $C_{6-10}$ aryl group and a $C_{1-6}$ alkoxy group;
a $C_{6-10}$ aryl group; or
a $C_{1-6}$ alkyl group optionally substituted by one or more substituents selected from the group consisting of a $C_{6-10}$ aryl group, a $C_{1-6}$ alkoxy-carbonyl group, a carboxyl group and a $C_{3-6}$ cycloalkyl group, and
$R_4$ is a hydrogen atom,
or a pharmaceutically acceptable salt thereof.

[11] A compound represented by the following formula:

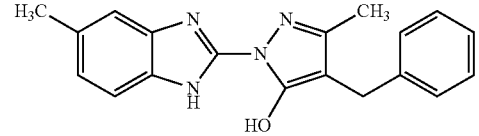 [SMILES: Cc1ccc2[nH]c(-n3nc(C)c(Cc4ccccc4)c3O)nc2c1]

or a pharmaceutically acceptable salt thereof.

[12] A PCA-1 inhibitor comprising a compound represented by the formula (I):

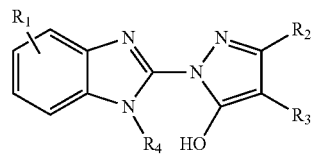

(I)

wherein $R_1$ is a hydrogen atom or a substituent; $R_2$ is a substituent; $R_3$ is a hydrogen atom or a substituent; and $R_4$ is a hydrogen atom or a substituent, or a pharmaceutically acceptable salt thereof.

[13] The inhibitor of the above-mentioned [12], wherein $R_1$ is
a hydrogen atom;
a $C_{1-6}$ alkyl group optionally substituted by a halogen atom;
a $C_{6-10}$ aryl group optionally substituted by one or more substituents selected from the group consisting of a halogen atom and a $C_{1-6}$ alkyl group; or a halogen atom,
R$_2$ is
a C$_{1-6}$ alkyl group or a C$_{6-10}$ aryl group,
R$_3$ is
a hydrogen atom;
a C$_{7-11}$ aralkyl group optionally substituted by one or more substituents selected from the group consisting of a halogen atom, a C$_{1-6}$ alkyl group optionally substituted by a halogen atom, a C$_{6-10}$ aryl group and a C$_{1-6}$ alkoxy group;
a C$_{6-10}$ aryl group; or
a C$_{1-6}$ alkyl group optionally substituted by one or more substituents selected from the group consisting of a C$_{6-10}$ aryl group, a C$_{1-6}$ alkoxy-carbonyl group, a carboxyl group and a C$_{3-6}$ cycloalkyl group, and
R$_4$ is a hydrogen atom.

[14] A PCA-1 inhibitor comprising a compound represented by the following formula:

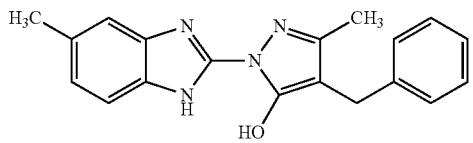 [SMILES: Cc1ccc2[nH]c(-n3nc(C)c(Cc4ccccc4)c3O)nc2c1]

or a pharmaceutically acceptable salt thereof.

[15] A prophylactic and/or therapeutic drug for a disease involving PCA-1, comprising a compound represented by the formula (I):

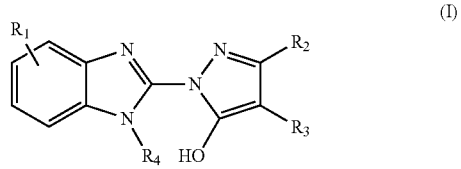

(I)

wherein R$_1$ is a hydrogen atom or a substituent; R$_2$ is a substituent; R$_3$ is a hydrogen atom or a substituent; and R$_4$ is a hydrogen atom or a substituent, or a pharmaceutically acceptable salt thereof, as an active ingredient.

[16] The prophylactic and/or therapeutic drug of the above-mentioned [15], wherein R$_1$ is
a hydrogen atom;
a C$_{1-6}$ alkyl group optionally substituted by a halogen atom;
a C$_{6-10}$ aryl group optionally substituted by one or more substituents selected from the group consisting of a halogen atom and a C$_{1-6}$ alkyl group; or
a halogen atom,
R$_2$ is
a C$_{1-6}$ alkyl group or a C$_{6-10}$ aryl group,
R$_3$ is
a hydrogen atom;
a C$_{7-11}$ aralkyl group optionally substituted by one or more substituents selected from the group consisting of a halogen atom, a C$_{1-6}$ alkyl group optionally substituted by a halogen atom, a C$_{6-10}$ aryl group and a C$_{1-6}$ alkoxy group;
a C$_{6-10}$ aryl group; or
a C$_{1-6}$ alkyl group optionally substituted by one or more substituents selected from the group consisting of a C$_{6-10}$ aryl group, a C$_{1-6}$ alkoxy-carbonyl group, a carboxyl group and a C$_{3-6}$ cycloalkyl group, and
R$_4$ is a hydrogen atom.

[17] A prophylactic and/or therapeutic drug for a disease involving PCA-1, comprising a compound represented by the following formula:

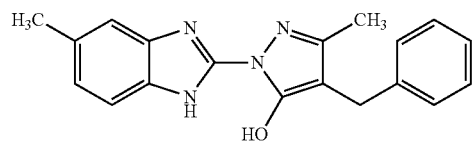 [SMILES: Cc1ccc2[nH]c(-n3nc(C)c(Cc4ccccc4)c3O)nc2c1]

or a pharmaceutically acceptable salt thereof.

[18] The prophylactic and/or therapeutic drug of the above-mentioned [17], wherein the disease involving PCA-1 is selected from the group consisting of cancer, a brain neurodegenerative disease and arteriosclerosis.

[19] The prophylactic and/or therapeutic drug of the above-mentioned [18], wherein the cancer is at least one kind selected from the group consisting of prostate cancer, pancreatic cancer and non-small cell lung cancer, which has an anticancer action against the above-mentioned cancers.

[20] A method for the prophylaxis and/or treatment of a disease involving PCA-1, comprising administering an effective amount of a compound represented by the formula (I):

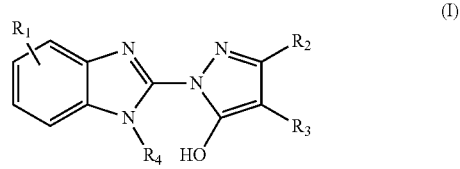

(I)

wherein R$_1$ is a hydrogen atom or a substituent; R$_2$ is a substituent; R$_3$ is a hydrogen atom or a substituent; and R$_4$ is a hydrogen atom or a substituent, or a pharmaceutically acceptable salt thereof, to a mammal.

[21] The method for the prophylaxis and/or treatment of the above-mentioned [20], wherein R$_1$ is
a hydrogen atom;
a C$_{1-6}$ alkyl group optionally substituted by a halogen atom;
a C$_{6-10}$ aryl group optionally substituted by one or more substituents selected from the group consisting of a halogen atom and a C$_{1-6}$ alkyl group; or
a halogen atom,
R$_2$ is
a C$_{1-6}$ alkyl group or a C$_{6-10}$ aryl group,
R$_3$ is
a hydrogen atom;
a C$_{7-11}$ aralkyl group optionally substituted by one or more substituents selected from the group consisting of a halogen atom, a C$_{1-6}$ alkyl group optionally substituted by a halogen atom, a C$_{6-10}$ aryl group and a C$_{1-6}$ alkoxy group;
a C$_{6-10}$ aryl group; or
a C$_{1-6}$ alkyl group optionally substituted by one or more substituents selected from the group consisting of a C$_{6-10}$ aryl group, a C$_{1-6}$ alkoxy-carbonyl group, a carboxyl group and a C$_{3-6}$ cycloalkyl group, and
R$_4$ is a hydrogen atom.

[22] A method for the prophylaxis and/or treatment of a disease involving PCA-1, comprising administering an effective amount of a compound represented by the following formula:

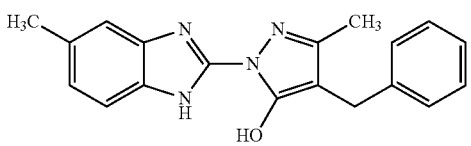 [SMILES: Cc1ccc2[nH]c(-n3nc(C)c(Cc4ccccc4)c3O)nc2c1]

or a pharmaceutically acceptable salt thereof, to a mammal.

[23] The method for the prophylaxis and/or treatment of the above-mentioned [22], wherein the disease involving PCA-1 is selected from the group consisting of cancer, a brain neurodegenerative disease and arteriosclerosis.

[24] The method for the prophylaxis and/or treatment of the above-mentioned [23], wherein the cancer is at least one kind selected from the group consisting of prostate cancer, pancreatic cancer and non-small cell lung cancer, which has an anticancer action against the above-mentioned cancers.

[25] The compound of any of the above-mentioned [1]-[11] or a pharmaceutically acceptable salt thereof for the prophylaxis or treatment of a disease involving PCA-1.

[26] The compound of the above-mentioned [25], wherein the disease involving PCA-1 is selected from the group consisting of cancer, a brain neurodegenerative disease and arteriosclerosis, or a pharmaceutically acceptable salt thereof.

[27] The compound of the above-mentioned [26], wherein the cancer is at least one kind selected from the group consisting of prostate cancer, pancreatic cancer and non-small cell lung cancer, which has an anticancer action against the above-mentioned cancers, or a pharmaceutically acceptable salt thereof.

In the following, a compound represented by the formula (I) (also to be referred to as compound (I)) and a pharmaceutically acceptable salt thereof are comprehensively referred to as the compound of the present invention.

Effect of the Invention

Since the compound of the present invention has a superior inhibitory action on the enzyme activity of PCA-1, it is useful for the prophylaxis and/or treatment of a disease involving PCA-1. Particularly, the compound of the present invention is useful as an anti-cancer agent for prostate cancer, pancreatic cancer, non-small cell lung cancer and the like. Moreover, it suppresses the growth of prostate cancer cell, pancreatic cancer cell, and non-small cell lung cancer cell in vitro.

BRIEF DESCRIPTION OF THE DRAWINGS

FIG. 1 is a graph showing an antitumor action of the compound of the present invention (Example 1) in a DU145 cell xenograft model.

DESCRIPTION OF EMBODIMENTS

The present invention is explained in the following. Unless particularly indicated, the terms used in the present specification have the meanings generally used in the field.

The terms used in the present specification are defined as follows.

Examples of the "halogen atom" include a fluorine atom, a chlorine atom, a bromine atom and an iodine atom.

The "$C_{1-6}$ alkyl group" means a straight chain or branched alkyl group having 1-6 carbon atoms, and specific examples thereof include methyl, ethyl, n-propyl, isopropyl, n-butyl, isobutyl, sec-butyl, tert-butyl, n-pentyl, isopentyl, tert-pentyl, neopentyl, 2-pentyl, 3-pentyl, n-hexyl, 2-hexyl and the like.

The "$C_{3-6}$ cycloalkyl group" means a cyclic alkyl group having 3-6 carbon atoms, and specific examples thereof include cyclopropyl, cyclobutyl, cyclopentyl, cyclohexyl and the like.

The "$C_{6-10}$ aryl group" means an aryl group having 6-10 carbon atoms, and specific examples thereof include phenyl, naphthyl and the like.

The "$C_{7-11}$ aralkyl group" means an arylalkyl group having 7-11 carbon atoms (an alkyl group substituted by an aryl group), and specific examples thereof include a benzyl group, a phenylethyl group, a phenylpropyl group, a naphthylmethyl group and the like.

The "$C_{1-6}$ alkoxy group" means a straight chain or branched alkoxy group having 1-6 carbon atoms, and specific examples thereof include methoxy, ethoxy, n-propoxy, isopropoxy, n-butoxy, isobutoxy, sec-butoxy, tert-butoxy, n-pentyloxy, isopentyloxy, tert-pentyloxy, neopentyloxy, 2-pentyloxy, 3-pentyloxy, n-hexyloxy, 2-hexyloxy and the like.

The "$C_{1-6}$ alkoxy group-carbonyl group" means a carbonyl group substituted by a $C_{1-6}$ alkoxy group (mentioned above), and specific examples thereof include methoxycarbonyl, ethoxycarbonyl, propoxycarbonyl, isopropoxycarbonyl, butoxycarbonyl, isobutoxycarbonyl, tert-butoxycarbonyl and the like.

As the substituent that the "$C_{1-6}$ alkyl group", "$C_{6-10}$ aryl group" and "$C_{7-11}$ aralkyl group" optionally have, a substituent selected from the group consisting of (1) a halogen atom (e.g., fluorine, chlorine, bromine, iodine; preferably fluorine),
(2) a lower alkyl group (e.g., a $C_{1-6}$ alkyl group such as methyl, ethyl, propyl, isopropyl, butyl, isobutyl, sec-butyl, tert-butyl, pentyl, hexyl, and the like, and the like),
(3) a cycloalkyl group (e.g., a $C_{3-6}$ cycloalkyl group such as cyclopropyl, cyclobutyl, cyclopentyl, cyclohexyl, and the like, and the like),
(4) a lower alkynyl group (e.g., a $C_{2-6}$ alkynyl group such as ethynyl, 1-propynyl, propargyl, and the like, and the like),
(5) a lower alkenyl group (e.g., a $C_{2-6}$ alkenyl group such as vinyl, allyl, isopropenyl, butenyl, isobutenyl, and the like, and the like),
(6) an aralkyl group (e.g., a $C_{7-12}$ aralkyl group such as benzyl, α-methylbenzyl, phenethyl, and the like, and the like),
(7) an aryl group (e.g., a $C_{6-10}$ aryl group such as phenyl, naphthyl, and the like, and the like, preferably a phenyl group),
(8) a lower alkoxy group (e.g., a $C_{1-6}$ alkoxy group such as methoxy, ethoxy, propoxy, isopropoxy, butoxy, isobutoxy, sec-butoxy, tert-butoxy, and the like, and the like),
(9) an aryloxy group (e.g., a $C_{6-10}$ aryloxy group such as phenoxy, and the like, and the like),
(10) a formyl group or a lower alkanoyl group (e.g., a $C_{1-6}$ alkyl-carbonyl group such as acetyl, propionyl, butyryl, isobutyryl, and the like, and the like),
(11) an arylcarbonyl group (e.g., a $C_{6-10}$ aryl-carbonyl group such as benzoyl, naphthoyl, and the like, and the like),
(12) a formyloxy group or a lower alkanoyloxy group (e.g., a $C_{1-6}$ alkyl-carbonyloxy group such as acetyloxy, propionyloxy, butyryloxy, isobutyryloxy, and the like, and the like),
(13) an arylcarbonyloxy group (e.g., a $C_{6-10}$ aryl-carbonyloxy group such as benzoyloxy, naphthoyloxy, and the like, and the like),
(14) a carboxyl group,
(15) a lower alkoxycarbonyl group (e.g., a $C_{1-6}$ alkoxy-carbonyl group such as methoxycarbonyl, ethoxycarbonyl, propoxycarbonyl, isopropoxycarbonyl, butoxycarbonyl, isobutoxycarbonyl, tert-butoxycarbonyl, and the like, and the like),
(16) an aralkyloxycarbonyl group (e.g., a $C_{7-12}$ aralkyloxycarbonyl group such as benzyloxycarbonyl, and the like, and the like),
(17) a carbamoyl group,
(18) a mono-, di- or tri-halogeno-lower alkyl group (e.g., a mono-, di- or tri-halogeno-$C_{1-6}$ alkyl group such as chloromethyl, dichloromethyl, trifluoromethyl, 2,2,2-trifluoroethyl, and the like, and the like),
(19) an oxo group,
(20) an amidino group,
(21) an imino group,
(22) an amino group,
(23) a mono-lower alkylamino group (e.g., a mono-$C_{1-6}$ alkylamino group such as methylamino, ethylamino, propylamino, isopropylamino, butylamino, and the like, and the like),
(24) a di-lower alkylamino group (e.g., a di-$C_{1-6}$ alkylamino group such as dimethylamino, diethylamino, dipropylamino, diisopropylamino, dibutylamino, N-ethyl-N-methylamino, and the like, and the like),
(25) a 3- to 8-membered nitrogen-containing heterocyclic group optionally having substituent(s) and optionally containing, besides carbon atom and one nitrogen atom, 1-3 hetero atoms selected from a nitrogen atom, an oxygen atom and a sulfur atom (e.g., a 3- to 8-membered nitrogen-containing heterocyclic group optionally having 1-5 substituents selected from a halogen atom, a nitro group, a cyano group, a hydroxy group, an optionally halogenated $C_{1-6}$ alkyl group, an optionally hal,ogenated $C_{1-6}$ alkoxy group, an amino group, a mono-$C_{1-6}$ alkylamino group, a di-$C_{1-6}$ alkylamino group, a carboxyl group, a $C_{1-6}$ alkyl-carbonyl group, a $C_{1-6}$ alkoxy-carbonyl group, a carbamoyl group, a mono-$C_{1-6}$ alkyl-carbamoyl group, a di-$C_{1-6}$ alkyl-carbamoyl group, a $C_{6-10}$ aryl-carbamoyl group, a $C_{6-10}$ aryl group, a $C_{6-10}$ aryloxy group, and an optionally halogenated $C_{1-6}$ alkyl-carbonylamino group, an oxo group and the like, and optionally containing, besides carbon atom and one nitrogen atom, 1-3 hetero atoms selected from a nitrogen atom, an oxygen atom and a sulfur atom; for example, aziridinyl, azetidinyl, pyrrolidinyl, pyridyl, pyrrolinyl, pyrrolyl, imidazolyl, pyrazolyl, imidazolidinyl, piperidyl, oxadiazolyl, isoxazolyl, morpholinyl, dihydropyridyl, tetrahydropyridyl, piperazinyl, N-methylpiperazinyl, N-ethylpiperazinyl and the like),
(26) an alkylenedioxy group (e.g., a $C_{1-3}$ alkylenedioxy group such as methylenedioxy, ethylenedioxy, and the like, and the like),
(27) a hydroxy group,
(28) a nitro group,
(29) a cyano group,
(30) a mercapto group,
(31) a sulfo group,
(32) a sulfino group,
(33) a phosphono group,
(34) a sulfamoyl group,
(35) a mono-lower alkylsulfamoyl group (e.g., a mono-$C_{1-6}$ alkylsulfamoyl group such as N-methylsulfamoyl, N-ethylsulfamoyl, N-propylsulfamoyl, N-isopropylsulfamoyl, N-butylsulfamoyl, and the like, and the like),
(36) a di-lower alkylsulfamoyl group (e.g., a di-$C_{1-6}$ alkylsulfamoyl group such as N,N-dimethylsulfamoyl, N,N-diethylsulfamoyl, N,N-dipropylsulfamoyl, N,N-dibutylsulfamoyl, and the like, and the like),
(37) a lower alkylthio group (e.g., a $C_{1-6}$ alkylthio group such as methylthio, ethylthio, propylthio, isopropylthio, butylthio, sec-butylthio, tert-butylthio, and the like, and the like),
(38) an arylthio group (e.g., a $C_{6-10}$ arylthio group such as phenylthio, naphthylthio, and the like, and the like),
(39) a lower alkylsulfinyl group (e.g., a $C_{1-6}$ alkylsulfinyl group such as methylsulfinyl, ethylsulfinyl, propylsulfinyl, butylsulfinyl, and the like, and the like),
(40) an arylsulfinyl group (e.g., a $C_{6-10}$ arylsulfinyl group such as phenylsulfinyl, naphthylsulfinyl, and the like, and the like),
(41) a lower alkylsulfonyl group (e.g., a $C_{1-6}$ alkylsulfonyl group such as methylsulfonyl, ethylsulfonyl, propylsulfonyl, butylsulfonyl, and the like, and the like),
(42) an arylsulfonyl group (e.g., a $C_{6-10}$ arylsulfonyl group such as phenylsulfonyl, naphthylsulfonyl, and the like, and the like),
(43) a lower alkylcarbonylamino group (e.g., a $C_{1-6}$ alkylcarbonylamino group such as methylcarbonylamino, and the like, and the like) and the like (to be referred to as substituent group A in the present specification) is used.

The compound represented by the formula (I) is explained below. Unless otherwise specified, the definition of each group is the same as that mentioned above.

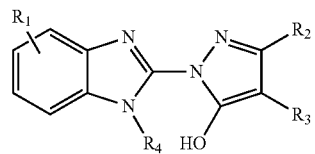

In the formula (I), $R_1$ is a hydrogen atom or a substituent. Here, examples of the "substituent" include an optionally substituted $C_{1-6}$ alkyl group, an optionally substituted $C_{6-10}$ aryl group, a halogen atom and the like. The substituents for $R_1$ may be those exemplified as the above-mentioned substituent group A. $R_1$ is preferably a hydrogen atom; a $C_{1-6}$ alkyl group (e.g., methyl, tert-butyl) optionally substituted by a halogen atom (e.g., fluorine atom); a $C_{6-10}$ aryl group (e.g., phenyl) optionally substituted by one or more substituents selected from the group consisting of a halogen atom (e.g., a chlorine atom) and a $C_{1-6}$ alkyl group (e.g., methyl); or a halogen atom (e.g., a chlorine atom). More preferably, $R_1$ is methyl.

In the formula (I), $R_2$ is a substituent. Here, examples of the "substituent" include an optionally substituted $C_{1-6}$ alkyl group, an optionally substituted $C_{6-10}$ aryl group and the like. The substituents for $R_2$ may be those exemplified as the above-mentioned substituent group A. $R_2$ is preferably an unsubstituted $C_{1-6}$ alkyl group (e.g., methyl) or an unsubstituted $C_{6-10}$ aryl group (e.g., phenyl). More preferably, $R_2$ is methyl.

In the formula (I), $R_3$ is a hydrogen atom or a substituent. Here, examples of the "substituent" include an optionally substituted $C_{7-11}$ aralkyl group, an optionally substituted $C_{6-10}$ aryl group, an optionally substituted $C_{1-6}$ alkyl group and the like. The substituents for $R_3$ may be those exemplified as the above-mentioned substituent group A. $R_3$ is preferably a hydrogen atom; a $C_{7-11}$ aralkyl group (e.g., benzyl, naphthylmethyl) optionally substituted by one or more substituents selected from the group consisting of a halogen atom (e.g., chlorine atom, fluorine atom), a $C_{1-6}$ alkyl group (e.g., methyl, tert-butyl) optionally substituted by a halogen atom (e.g., fluorine atom), a $C_{6-10}$ aryl group (e.g., phenyl) and a $C_{1-6}$ alkoxy group (e.g., methoxy); a $C_{6-10}$ aryl group (e.g., phenyl); or a $C_{1-6}$ alkyl group (e.g., methyl, hexyl) optionally substituted by one or more substituents selected from the group consisting of a $C_{6-10}$ aryl group (e.g., phenyl), a $C_{1-6}$ alkoxy-carbonyl group (e.g., methoxycarbonyl), a carboxyl group and a $C_{3-6}$ cycloalkyl group (e.g., cyclohexyl). More preferably, $R_3$ is benzyl.

In the formula (I), $R_4$ is a hydrogen atom or a substituent. Here, examples of the "substituent" include an optionally substituted 01-6 alkyl group and the like. The substituents for $R_4$ may be those exemplified as the above-mentioned substituent group A. $R_4$ is preferably a hydrogen atom.

Of the compounds represented by the formula (I), particularly preferred is a compound wherein $R_1$ is
a hydrogen atom;
a $C_{1-6}$ alkyl group optionally substituted by a halogen atom (e.g., methyl, tert-butyl, trifluoromethyl);
a $C_{6-10}$ aryl group optionally substituted by one or more substituents selected from the group consisting of a halogen atom and a $C_{1-6}$ alkyl group (e.g., phenyl, methylphenyl, chlorophenyl); or
a halogen atom (e.g., chlorine atom), $R_2$ is
a $C_{1-6}$ alkyl group (e.g., methyl) or a $C_{6-10}$ aryl group (e.g., phenyl), $R_3$ is
a hydrogen atom;
a $C_{7-11}$ aralkyl group optionally substituted by one or more substituents selected from the group consisting of a halogen atom, a $C_{1-6}$ alkyl group optionally substituted by a halogen atom, a $C_{6-10}$ aryl group, and a $C_{1-6}$ alkoxy group (e.g., benzyl, naphthylmethyl, tert-butylbenzyl, fluorobenzyl, chlorobenzyl, dichlorobenzyl, trifluoromethylbenzyl, phenylbenzyl, methoxybenzyl);
a $C_{6-10}$ aryl group (e.g., phenyl); or
a $C_{1-6}$ alkyl group optionally substituted by one or more substituents selected from the group consisting of a $C_{1-6}$ alkoxy-carbonyl group, a carboxyl group, and a $C_{3-6}$ cycloalkyl group (e.g., methyl, hexyl, methoxycarbonylmethyl, carboxymethyl, diphenylmethyl), and
$R_4$ is a hydrogen atom.

Of compounds (I), still more preferred is a compound represented by

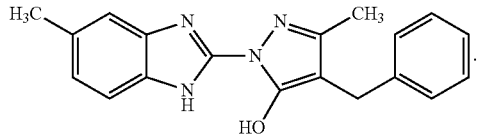 [SMILES: Cc1ccc2[nH]c(-n3nc(C)c(Cc4ccccc4)c3O)nc2c1]

Among compounds (I), particularly, a compound wherein $R_3$ is not methyl when $R_1$ is a hydrogen atom, and a compound wherein $R_3$ is not a hydrogen atom when $R_1$ is a substituent are novel compounds.

As a salt of compound (I), a pharmaceutically acceptable salt and the like can be mentioned. Examples containing include an acid addition salt with an acid such as trifluoroacetic acid, acetic acid, lactic acid, succinic acid, maleic acid, tartaric acid, citric acid, gluconic acid, ascorbic acid, benzoic acid, methanesulfonic acid, p-toluenesulfonic acid, cinnamic acid, fumaric acid, phosphonic acid, hydrochloric acid, nitric acid, hydrobromic acid, hydroiodic acid, sulfamic acid, sulfuric acid and the like; salts with metal such as sodium, potassium, magnesium, calcium and the like; a salt with an organic base such as trimethylamine, triethylamine, pyridine, picoline, N-methylpyrrolidine, N-methylpiperidine, N-methylmorpholine and the like, and the like.

When compound (I) has an isomer such as optical isomer, stereoisomer, positional isomer, rotamer and the like, any one of the isomers and a mixture of isomers are also encompassed in compound (I). For example, when compound (I) has an optical isomer, an optical isomer resolved from the racemate is also encompassed in compound (I). These isomers can be each obtained as a single product by a synthesis method, and a separation method (concentration, solvent extraction, column chromatography, recrystallization etc.) known per se. Also, compound (I) contains a structural isomer such as tautomer and the like and a geometric isomer. Such isomers are also within the scope of the present invention.

Examples of the tautomer include the following structures.

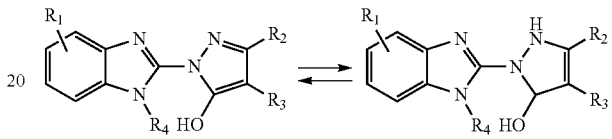

wherein each symbol is as defined above.

Compound (I) may be a crystal or an amorphous form. When compound (I) is a crystal, the crystal is encompassed in compound (I), whether the crystal form is single or mixture of crystal forms. Crystals can be produced by crystallization by applying a crystallization method known per se.

Compound (I) may be a solvate (e.g., hydrate etc.) or a non-solvate, both of which are encompassed in compound (I).

Compound (I) may be labeled with an isotope (e. $^3$H, $^{14}$C, $^{35}$S, $^{125}$I etc.) and the like.

The compound of the present invention has a Prostate Cancer Antigen-1 (PCA-1) binding activity, and has an action to inhibit the enzyme activity of PCA-1. PCA-1 is a gene highly expressed specifically in prostate cancer and identified by the present inventors. Since this gene has a high homology to *Escherichia coli* protein AlkB, which is a DNA, RNA alkylation damage repair enzyme, it is also called human AlkB homologue 3 (hALKBH3), and has recently been confirmed to catalyze DNA, RNA demethylation like AlkB. To inhibit the enzyme activity of PCA-1 means to directly and/or indirectly inhibit DNA, RNA demethylation reaction of PCA-1. For example, the enzyme activity is inhibited by specifically binding to PCA-1. The enzyme activity can be measured according to the method generally performed in the field, or said method modified as necessary. For example, it can be evaluated by measuring the degree of demethylation by using a methylated substrate DNA.

Due to the superior PCA-1 inhibitory activity of the compound of the present invention, the compound of the present invention is useful as a prophylactic or therapeutic drug for a disease, for which PCA-1 is involved in the onset and progression thereof (disease wherein onset or progression is promoted), in mammals (e.g., human, monkey, cat, swine, horse, bovine, mouse, rat, guinea pig, dog, rabbit etc.).

Examples of such disease include cancer (e.g., prostate cancer, pancreatic cancer, non-small cell lung cancer), brain neurodegenerative disease (e.g., Alzheimer, Parkinson), arteriosclerosis and the like.

The content of the compound of the present invention in a medicament (for example, anti-cancer agent etc.) containing the compound of the present invention as an active ingredient is generally about 0.01-about 99.9 wt %, preferably about 0.1-about 50 wt %, relative to the whole preparation.

The dose of the compound of the present invention is determined in consideration of the age, body weight, general health condition, sex, diet, administration time, administration method, clearance rate, combination of drugs, and the level of the disease state for which the patient is receiving the treatment then, or other factors.

While the dose varies depending on the target disease, symptom, subject of administration, administration method and the like, for example, the compound of the present invention is preferably administered in about 0.1 100 mg/kg (body weight), preferably about 1-10 mg/kg (body weight), more preferably about 1-3 mg/kg (body weight), as the amount of compound (I), in once or 2 or 3 portions per day.

The compound of the present invention can be used in combination with other drugs according to the target disease. Such combination drug may be a low-molecular-weight compound, or a high-molecular-weight protein, polypeptide, antibody or vaccine and the like. In this case, the administration period of the compound of the present invention and the combination drug is not limited, and the compound of the present invention and the combination drug only need to be combined at the time of administration.

The compound of the present invention can be appropriately formulated as a solid preparation such as tablet, capsule, granule, powder and the like; liquid preparation such as syrup, injection and the like; a percutaneous absorber such as adhesive preparation, ointment, plaster and the like; inhalant; or suppository, by blending with a pharmaceutically acceptable carrier.

A medicament containing the compound of the present invention is administered orally or parenterally, wherein only one kind of the above-mentioned compound may be used singly, or two or more kinds thereof may be used in combination.

As the pharmaceutically acceptable carrier, various organic or inorganic carrier substances conventionally used as preparation materials can be used. Specifically, excipient, lubricant, binder, disintegrant for solid preparations, solvent, solubilizing agents, suspending agent, isotonic agent, buffering agent, soothing agent for liquid preparations and the like can be blended. Also, where necessary, preparation additives such as preservative, antioxidant, colorant, sweetening agent and the like can also be used.

Examples of the excipient include lactose, sucrose, glucose, starch, saccharose, crystalline cellulose, *Glycyrrhiza uralensis*, mannitol, sodium hydrogen carbonate, calcium phosphate, calcium sulfate and the like.

Examples of the lubricant include magnesium stearate, stearic acid, calcium stearate, purification talc, colloidal silica and the like.

Examples of the binder include crystalline cellulose, sucrose, mannitol, dextrin, hydroxypropylcellulose, hydroxypropylmethylcellulose, polyvinylpyrrolidone and the like.

Examples of the disintegrant include starch, carboxymethylcellulose, calcium carboxymethylcellulose, croscarmellose sodium, sodium carboxymethyl starch and the like.

Preferable examples of the solvent include water for injection, alcohol, propylene glycol, macrogol, sesame oil, corn oil and the like.

Preferable examples of the solubilizing agents include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyltriethanolamine, sodium lauryl sulfate, lauryl aminopropionic acid, lecithin, benzalkonium chloride, benzethonium chloride, glycerol monostearate and the like; polyvinyl alcohol, polyvinylpyrrolidone, sodium carboxymethylcellulose, methylcellulose, hydroxymethylcellulose, hydroxyethylcellulose, hydroxypropylcellulose and the like.

Preferable examples of the isotonic agent include sodium chloride, glycerol, D-mannitol and the like.

Preferable examples of the buffering agent include buffer such as phosphate, acetate, carbonate and citrate and the like, and the like.

Preferable examples of the soothing agent include benzylalcohol and the like.

Preferable examples of the preservative include paraoxybenzoates, chlorobutanol, benzyl alcohol, phenethyl alcohol, dehydroacetic acid, sorbic acid and the like.

Preferable examples of the antioxidant include sulfite, ascorbic acid and the like.

Preferable examples of the colorant include tar pigment, caramel, red ferric oxide, titanium oxide, riboflavins and the like.

Preferable examples of the sweetening agent include glucose, fructose, invert sugar, sorbitol, xylitol, glycerol, simple syrup and the like.

Production Method

The compound represented by the formula (I), an isomer thereof, a solvate and a pharmaceutically acceptable salt thereof of the present invention can be produced by utilizing the features based on the basic skeleton or the kind of substituents and applying various known synthesis methods. For example, they can be produced according to, but not limited to, the following synthesis methods, which can be appropriately modified when desired. As such modification, alkylation, acylation, amination, imination, halogenation, reduction, oxidation and the like can be mentioned, and the reaction or method generally used in the field is utilized. In this case, it is sometimes effective for the production technique to replace, depending on the kind of the functional group, the functional group with a suitable protecting group (group easily converted to the functional group), in the stage of a starting material or an intermediate. The chemical property of the protecting group, the method of introduction thereof, and removal thereof are described in detail in, for example, T. Greene and P. Wuts "Protective Groups in Organic Synthesis" ($3^{rd}$ ed.), John Wiley & Sons NY (1999).

The starting compounds may be, unless particularly indicated, products which are easily available commercially, or can be produced according to a method known per se or a method analogous thereto.

In each reaction and each reaction for the synthesis of starting compounds, generally known solvents may be used for the reaction.

Examples of the generally known solvents include ethers such as tetrahydrofuran, diethyl ether, 1,2-dimethoxyethane, 1,4-dioxane and the like, esters such as ethyl acetate, butyl acetate and the like, aromatic hydrocarbons such as benzene, toluene and the like, aromatic heterocycle compounds such as pyridine, lutidine and the like, amides such as N,N-dimethylformamide, N-methylpyrrolidone and the like, halides such as chloroform, methylene chloride and the like, alcohols such as methanol, ethanol, 2-propanol, 2,2-dimethylethanol and the like, hydrocarbon compounds such as hexane, heptane, petroleum ether and the like, carboxylic acids such as formic acid, acetic acid and the like, or water and the like.

The solvent to be used for the reaction may be a single solvent or a mixture of 2 to 6 kinds of solvents.

Also, reactions are sometimes performed in the co-presence of an amine such as triethylamine, N,N-diisopropylamine, pyridine, N-methylmorpholine and the like, or a base such as sodium hydroxide, potassium carbonate and the like.

Also, reactions are sometimes performed in the co-presence of, for example, an acid such as hydrochloric acid, sulfuric acid, acetic acid and the like.

Production Method 1

The synthesis scheme of the compound of the present invention is shown below (detailed reactions follow Examples). In the scheme, a specific group or compound is described. It is clear to those of ordinary skill in the art that substitutable groups and compounds can be used.

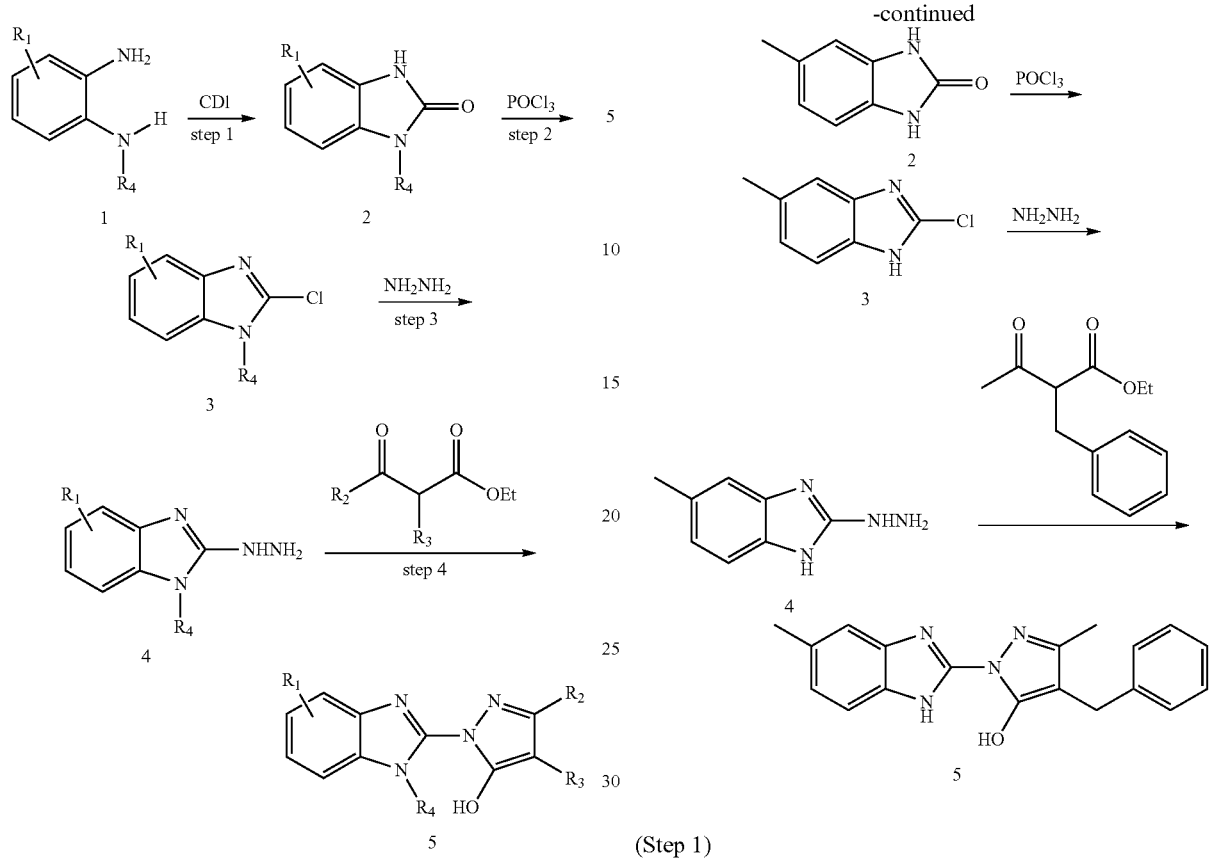

wherein Et is ethyl and each of other symbols is as defined above.

In step 1, a benzimidazolone skeleton is formed via a cyclization reaction. Such cyclization reaction can be performed by a reaction with a reagent such as carbonyldiimidazole (CDI) and the like.

In steps 2 and 3, a hydrazino group is introduced into the benzimidazole skeleton. This reaction can be performed by chlorinating with a chlorinating agent such as phosphoryl chloride and the like, followed by a reaction with hydrazine.

In step 4, a ring is further formed by a reaction of a hydrazine derivative with ketone.

All of them are performed by the methods generally carried out in the field and an appropriate combination thereof.

EXAMPLES

The present invention is explained in detail in the following by referring to Examples which are not to be construed as limitative. The reagents and materials to be used are commercially available unless particularly limited.

Example 1

Synthesis of 1-(5-methyl-1H-benzimidazol-2-yl)-3-methyl-4-(phenylmethyl)-1H-pyrazol-5-ol

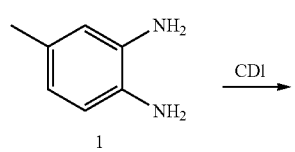

(Step 1)

Synthesis of 5-methyl-1,3-dihydrobenzimidazol-2-one (2)

To a solution of 4-methyl-1,2-phenylenediamine (1) (25 g) in tetrahydrofuran (375 mL) was added dropwise a solution of 1,1'-carbonyldiimidazole (36.5 g) in dichloromethane (375 mL). After stirring at room temperature for 6.5 hr, diisopropylether (375 mL) was added to the reaction mixture. After stirring at room temperature, the resulting precipitate was collected by filtration. The precipitate was washed with diisopropyl ether, and dried under reduced pressure to give 5-methyl-1,3-dihydrobenzimidazol-2-one (2) (24.6 g).

ESI-HRMS (positive ion, sodium formate): calcd for $C_8H_8N_2ONa([M+Na]^+)$ 171.0529. found 171.0529

NMR (DMSO-$d_6$, δ): 2.27 (3H, s), 6.70-6.81 (3H, m), 10.46 (2H, br s)

(Step 2)

Synthesis of 2-chloro-5-methyl-1H-benzimidazole (3)

A mixture of 5-methyl-1,3-dihydrobenzimidazol-2-one (2) (24.4 g) and phosphoryl chloride (245 mL) was stirred at 90° C. for 5 hr. After cooling to room temperature, chloroform (250 mL) was added to the reaction mixture. After stirring at room temperature, the resulting precipitate was collected by filtration, and washed 5 times with chloroform (100 mL). To the precipitate was added a mixture of ethyl acetate and saturated sodium hydrogen carbonate solution. After stirring at room temperature, the organic phase was successively washed with water and brine, and dried over magnesium sulfate. The solvent was evaporated under reduced pressure. The residue was powdered with hexane and diisopropyl ether to give 2-chloro-5-methyl-1H-benzimidazole (3) (20.4 g).

ESI-HRMS (positive ion, sodium formate): calcd for $C_8H_8ClN_2([M+H]^+)$ 167.0371. found 167.0391

NMR (DMSO-$d_6$, δ): 2.40 (3H, s), 7.00-7.06 (1H, m), 7.29 (1H, s), 7.39 (1H, d, J=8.2 Hz)

(Step 3)

Synthesis of
2-hydrazino-5-methyl-1H-benzimidazole (4)

A mixture of 2-chloro-5-methyl-1H-benzimidazole (3) (10.2 g) and hydrazine 1 hydrate (59 mL) was stirred at 100° C. for 4 hr. After cooling to room temperature, water (60 mL) was added to the reaction mixture. After stirring under ice-cooling, the resulting precipitate was collected by filtration. The precipitate was washed three times, and then dried under reduced pressure to give 2-hydrazino-5-methyl-1H-benzimidazole (4) (8.4 g).

ESI-HRMS (positive ion, sodium formate): calcd for $C_8H_{11}N_4([M+H]^+)$ 163.0978. found 163.0985

NMR (DMSO-$d_6$, δ): 2.30 (3H, s), 4.39 (2H, br s), 6.63-6.70 (1H, m), 6.91-6.94 (1H, m), 6.97-7.01 (1H, m), 7.69 (1H, br s), 10.87 (1H, br s)

(Step 4)

Synthesis of 3-methyl-1-(5-methyl-1H-benzimidazol-2-yl)-4-(phenylmethyl)-1H-pyrazol-5-ol (5)

A mixture of 2-hydrazino-5-methyl-1H-benzimidazole (4) (1.0 g) and ethyl 2-acetyl-3-phenylpropanoate (1.4 mL) in acetic acid (20 mL) was stirred at room temperature for 2 hr. The reaction mixture was added to a mixture of acetonitrile (100 mL) and water (100 mL). After stirring at room temperature, the resulting precipitate was collected by filtration, and washed with a mixture of acetonitrile and water (1:1). The precipitate was recrystallized from ethanol (95 mL) to give 3-methyl-1-(5-methyl-1H-benzimidazol-2-yl)-4-(phenylmethyl)-1H-pyrazol-5-ol (5) (0.64 g).

ESI-HRMS (positive ion, sodium formate): calcd for $C_{19}H_{19}N_4O([M+H]^+)$ 319.1559. found 319.1588

NMR (DMSO-$d_6$, δ): 2.15 (3H, s), 2.39 (3H, s), 3.59 (2H, s), 6.96-7.00 (1H, m), 7.13-7.20 (1H, m), 7.23-7.29 (4H, m), 7.31 (1H, br s), 7.39 (1H, d, J=8.2 Hz)

IR(KBr): 3312, 3024, 2936, 2915, 1653, 1553 cm$^{-1}$

Melting point: 205-208° C.

HPLC retention time: 11.2 min

HPLC gradient condition: $CH_3CN$/0.1% TFA; $CH_3CN$ (%)/min: 10/0, 10/1, 90/11, 90/15, 10/15.1, 10/20

Example 2

Synthesis of 3-methyl-1-(4-methyl-1H-benzimidazol-2-yl)-4-(phenylmethyl)-1H-pyrazol-5-ol (10)

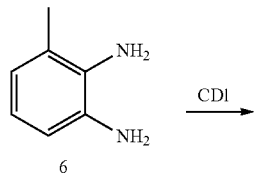

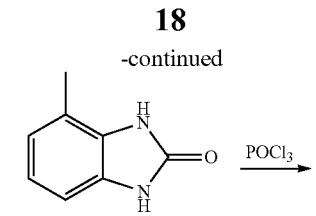

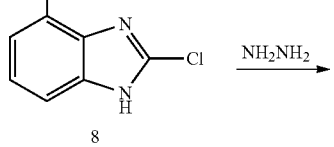

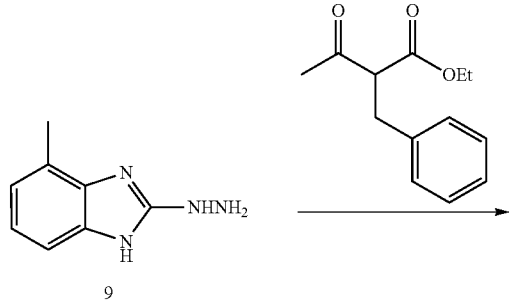

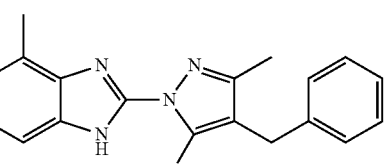

(Step 1)

Synthesis of
4-methyl-1,3-dihydrobenzimidazol-2-one (7)

Using 3-methyl-1,2-phenylenediamine (6) and by a method similar to that in Example 1, step 1, 4-methyl-1,3-dihydrobenzimidazol-2-one (7) was obtained.

ESI-HRMS (positive ion, sodium formate): calcd for $C_8H_8N_2ONa([M+Na]^+)$ 171.0529. found 171.0529

NMR (MeOH-$d_4$, δ): 2.33 (3H, s), 6.83 (1H, d, J=7.8 Hz), 6.86 (1H, d, J=7.4 Hz), 6.89-6.95 (1H, m)

(Step 2)

Synthesis of 2-chloro-4-methyl-1H-benzimidazole (8)

Using 4-methyl-1,3-dihydrobenzimidazol-2-one (7) and by a method similar to that in Example 1, step 2, 2-chloro-4-methyl-1H-benzimidazole (8) was obtained.

ESI-HRMS (positive ion, sodium formate): calcd for $C_8H_7ClN_2([M+H]^+)$ 167.0370. found 167.0375

NMR (MeOH-$d_4$, δ): 2.50 (3H, s), 7.04 (1H, d, J=7.4 Hz), 7.11-7.17 (1H, m), 7.30 (1H, d, J=8.2 Hz)

(Step 3)

Synthesis of
2-hydrazino-4-methyl-1H-benzimidazole (9)

Using 2-chloro-4-methyl-1H-benzimidazole (8) and by a method similar to that in Example 1, step 3, 2-hydrazino-4-methyl-1H-benzimidazole (9) was obtained.

ESI-HRMS (positive ion, sodium formate): calcd for $C_8H_{10}N_4([M+H]^+)$ 163.0978. found 163.1009

NMR (MeOH-$d_4$, δ): 2.43 (3H, s), 6.79 (1H, d, J=7.3 Hz), 6.84-6.91 (1H, m), 7.06 (1H, d, J=7.8 Hz)
(Step 4)

3-methyl-1-(4-methyl-1H-benzimidazol-2-yl)-4-(phenylmethyl)-1H-pyrazol-5-ol (10)

Using 2-hydrazino-4-methyl-1H-benzimidazole (9) and in the same manner as in Example 1, step 4, 3-methyl-1-(4-methyl-1H-benzimidazol-2-yl)-4-(phenylmethyl)-1H-pyrazol-5-ol (10) was obtained.
ESI-HRMS (positive ion, sodium formate): calcd for $C_{19}H_{19}N_4O([M+H]^+)$ 319.1559. found 319.1562
NMR (DMSO-$d_6$, δ): 2.18 (3H, s), 2.52 (3H, s), 3.61 (2H, s), 6.95-6.99 (1H, m), 7.05 (1H, t, J=7.8 Hz), 7.13-7.21 (1H, m), 7.22-7.30 (4H, m), 7.35 (1H, d, 3=7.8 Hz)
IR(KBr): 3272, 3027, 1667, 1628, 1575 cm$^{-1}$
HPLC retention time: 11.9 min Example 3

Synthesis of 1-(5-chloro-1H-benzimidazol-2-yl)-3-methyl-4-(phenylmethyl)-1H-pyrazol-5-ol (15)

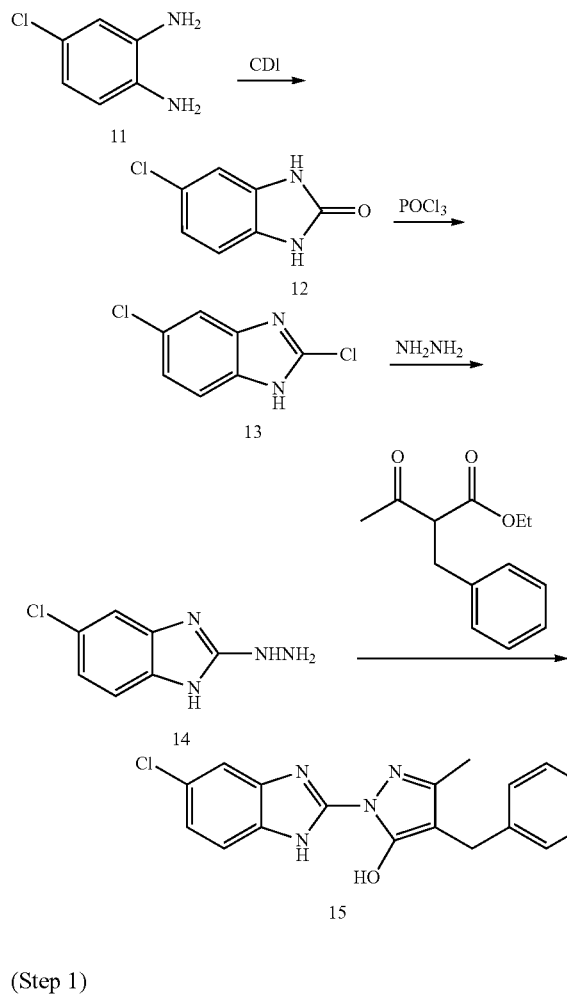

(Step 1)

Synthesis of 5-chloro-1,3-dihydrobenzimidazol-2-one (12)

Using 4-chloro-1,2-phenylenediamine (11) and by a method similar to that in Example 1, step 1, 5-chloro-1,3-dihydrobenzimidazol-2-one (12) was obtained.

ESI Mass: 191.0[M+Na]$^+$ (positive)
NMR (DMSO-$d_6$, δ): 6.89-6.97 (3H, m), 10.75 (2H, br s)
(Step 2)

Synthesis of 2,5-dichloro-1H-benzimidazole (13)

Using 5-chloro-1,3-dihydrobenzimidazol-2-one (12) and by a method similar to that in Example 1, step 2, 2,5-dichloro-1H-benzimidazole (13) was obtained.
ESI Mass: 187.0[M+H]$^+$ (positive)
NMR (MeOH-$d_4$, δ): 7.26 (1H, dd, J=1.8 and 8.7 Hz), 7.46 (1H, d, J=8.7 Hz), 7.51 (1H, d, J=1.8 Hz)
(Step 3)

Synthesis of 5-chloro-2-hydrazino-1H-benzimidazole (14)

Using 2,5-dichloro-1H-benzimidazole (13) and by a method similar to that in Example 1, step 3, 5-chloro-2-hydrazino-1H-benzimidazole (14) was obtained.
ESI-HRMS (positive ion, sodium formate): calcd for $C_7H_8ClN_4([M+H]^+)$ 183.0432. found 183.0442
NMR (DMSO-$d_6$, δ): 4.49 (2H, br s), 6.76-6.93 (1H, m), 7.03-7.14 (2H, m), 7.98 (1h, br s), 11.15 (1H, br s)
(Step 4)

Synthesis of 1-(5-chloro-1H-benzimidazol-2-yl)-3-methyl-4-(phenylmethyl)-1H-pyrazol-5-ol (15)

Using 5-chloro-2-hydrazino-1H-benzimidazole (14) and in the same manner as in Example 1, step 4, 1-(5-chloro-1H-benzimidazol-2-yl)-3-methyl-4-(phenylmethyl)-1H-pyrazol-5-ol (15) was obtained.
ESI-HRMS (positive ion, sodium formate): calcd for $C_{18}H_{16}ClN_4O([M+H]^+)$ 339.1007. found 339.0978
NMR (DMSO-$d_6$, δ): 2.17 (3H, s), 3.59 (2H, s), 7.13-7.21 (2H, m), 7.24-7.30 (4H, m), 7.52 (1H, d, J=8.7 Hz), 7.55 (1H, d, J=2.3 Hz)
IR(KBr): 3263, 3031, 2914, 2842, 1654, 1623, 1556 cm$^{-1}$
HPLC retention time: 13.1 min Example 4

Synthesis of 3-methyl-4-(phenylmethyl)-1-(5-trifluoromethyl-1H-benzimidazol-2-yl)-1H-pyrazol-5-ol (20)

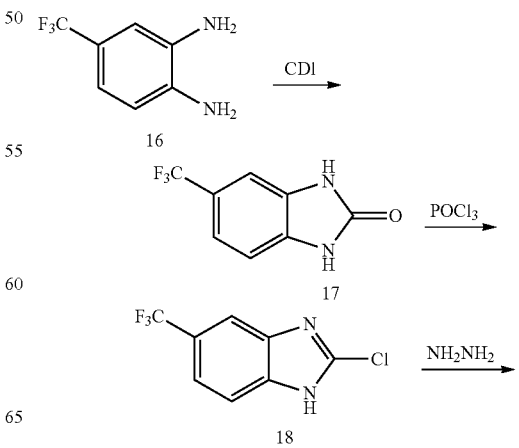

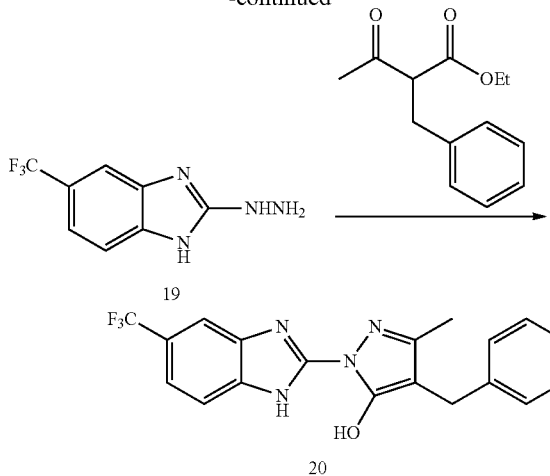

(Step 1)

Synthesis of 5-trifluoromethyl-1,3-dihydrobenzimidazol-2-one (17)

Using 4-trifluoromethyl-1,2-phenylenediamine (16) and by a method similar to that in Example 1, step 1,5-trifluoromethyl-1,3-dihydrobenzimidazol-2-one (17) was obtained.

ESI Mass: 225.0[M+Na]$^+$ (positive)
NMR (DMSO-d$_6$, δ): 7.08 (1H, d, J=8.2 Hz), 7.15 (1H, s), 7.28 (1H, d, J=8.2 Hz), 10.99 (2H, br s)

(Step 2)

Synthesis of 2-chloro-5-trifluoromethyl-1H-benzimidazole (18)

Using 5-trifluoromethyl-1,3-dihydrobenzimidazol-2-one (17) and by a method similar to that in Example 1, step 2, 2-chloro-5-trifluoromethyl-1H-benzimidazole (18) was obtained.

ESI-HRMS (positive ion, sodium formate): calcd for C$_8$H$_5$ClF$_3$N$_2$([N+H]$^+$) 221.0088. found 221.0098
NMR (DMSO-d$_6$, δ): 7.54 (1H, d, J=8.2 Hz), 7.70 (1H, d, J=8.2 Hz), 7.88 (1H, s)

(Step3)

Synthesis of 2-hydrazino-5-trifluoromethyl-1H-benzimidazole (19)

Using 2-chloro-5-trifluoromethyl-1H-benzimidazole (18) and by a method similar to that in Example 1, step 3,2-hydrazino-5-trifluoromethyl-1H-benzimidazole (19) was obtained.

ESI-HRMS (positive ion, sodium formate); calcd for C$_8$H$_8$F$_3$N$_4$([M+H]$^+$) 217.0696. found 217.0692
NMR (MeOH-d$_4$, δ): 7.25-7.39 (2H, m), 7.48-7.53 (1H, m)

(Step 4)

Synthesis of 3-methyl-4-(phenylmethyl)-1-(5-trifluoromethyl-1H-benzimidazol-2-yl)-1H-pyrazol-5-ol (20)

Using 2-hydrazino-5-trifluoromethyl-1H-benzimidazole (19) and in the same manner as in Example 1, step 4, 3-methyl-4-(phenylmethyl)-1-(5-trifluoromethyl-1H-benzimidazol-2-yl)-1H-pyrazol-5-ol (20) was obtained.

ESI-HRMS (positive ion, sodium formate); calcd for C$_{19}$H$_{16}$F$_3$N$_4$O([M+H]$^+$) 373.1271. found 373.1259
NMR (DMSO-d$_6$, δ): 2.19 (3H, s), 3.60 (2H, s), 7.14-7.21 (1H, m), 7.24-7.31 (4H, m), 7.46-7.52 (1H, m), 7.70 (1H, d, J=8.2 Hz), 7.84 (1H, s)
IR(KBr): 3033, 2935, 2901, 1637, 1551 cm$^{-1}$
HPLC retention time: 13.6 min

Example 5

Synthesis of 1-[5-(1,1-dimethylethyl)-1H-benzimidazol-2-yl]-3-methyl-4-(phenylmethyl)-1H-pyrazol-5-ol (25)

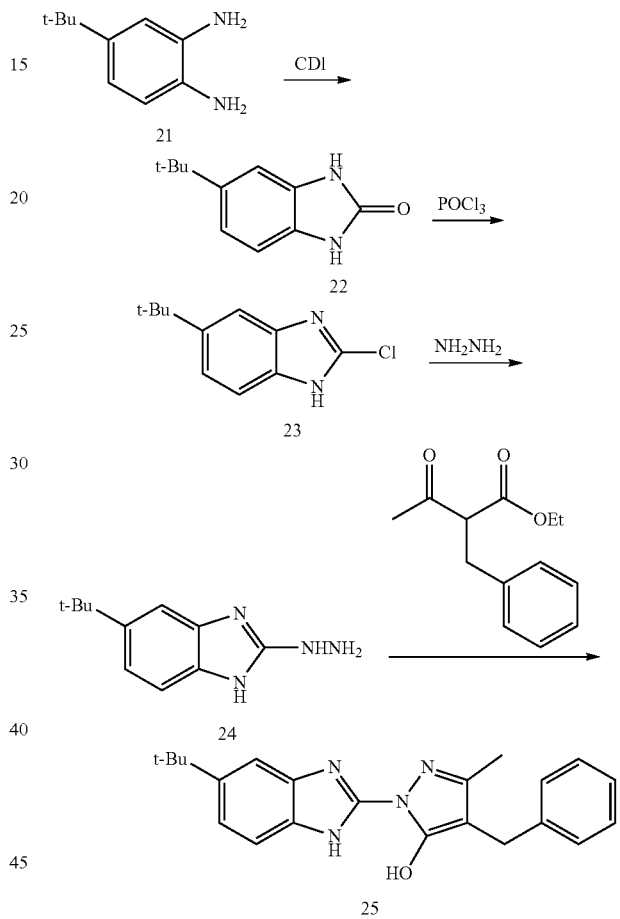

(Step 1)

Synthesis of 5-(1,1-dimethylethyl)-1,3-dihydrobenzimidazol-2-one (22)

Using 4-(1,1-dimethylethyl)-1,2-phenylenediamine (21) and by a method similar to that in Example 1, step 1, 5-(1,1-dimethylethyl)-1,3-dihydrobenzimidazol-2-one (22) was obtained.

ESI Mass: 191.1[M+H]$^+$ (positive)
NMR (DMSO-d$_5$, δ): 1.26 (9H, s), 6.83 (1H, d, J=7.8 Hz), 6.91 (1H, s), 6.94-6.97 (1H, m), 10.44 (2H, br s)

(Step 2)

Synthesis of 2-chloro-5-(1,1-dimethylethyl)-1H-benzimidazole (23)

Using 5-(1,1-dimethylethyl)-1,3-dihydrobenzimidazol-2-one (22) and by a method similar to that in Example 1, step 2, 2-chloro-5-(1,1-dimethylethyl)-1H-benzimidazole (23) was obtained.

ESI Mass: 209.1[M+H]$^+$ (positive)
NMR (DMSO-d$_6$, δ): 1.31 (9H, s), 7.25-7.44 (3H, m)
(Step 3)

Synthesis of 5-(1,1-dimethylethyl)-2-hydrazino-1H-benzimidazole (24)

Using 2-chloro-5-(1,1-dimethylethyl)-1H-benzimidazole (23) and by a method similar to that in Example 1, step 3, 5-(1,1-dimethylethyl)-2-hydrazino-1H-benzimidazole (24) was obtained.

ESI-HRMS (positive ion, sodium formate): calcd for C$_{11}$H$_{17}$N$_4$([M+H]$^+$) 205.1448. found 205.1458

NMR (DMSO-d$_6$, δ): 1.29 (9H, s), 6.87-7.95 (3H, m)
(Step 4)

Synthesis of 1-[5-(1,1-dimethylethyl)-1H-benzimidazol-2-yl]-3-methyl-4-(phenylmethyl)-1H-pyrazol-5-ol (25)

Using 5-(1,1-dimethylethyl)-2-hydrazino-1H-benzimidazole (24) and in the same manner as in Example 1, step 4, 1-[5-(1,1-dimethylethyl)-1H-benzimidazol-2-yl]-3-methyl-4-(phenylmethyl)-1H-pyrazol-5-ol (25) was obtained.

ESI-HRMS (positive ion, sodium formate): calcd for C$_{22}$H$_{25}$N$_4$O([M+H]$^+$) 361.2023. found 361.2029

NMR (DMSO-d$_6$, δ): 1.33 (9H, s), 2.15 (3H, s), 3.59 (2H, s), 7.13-7.20 (1H, m), 7.22-7.30 (5H, m), 7.43 (1H, d, J=8.2 Hz), 7.51 (1H, br s)

IR(KBr): 3026, 2961, 2903, 1655, 1558 cm$^{-1}$

HPLC retention time: 12.5 min

Example 6

Synthesis of 1-(4,5-dimethyl 1H-benzimidazol-2-yl)-3-methyl-4-(phenylmethyl)-1H-pyrazol-5-ol (30)

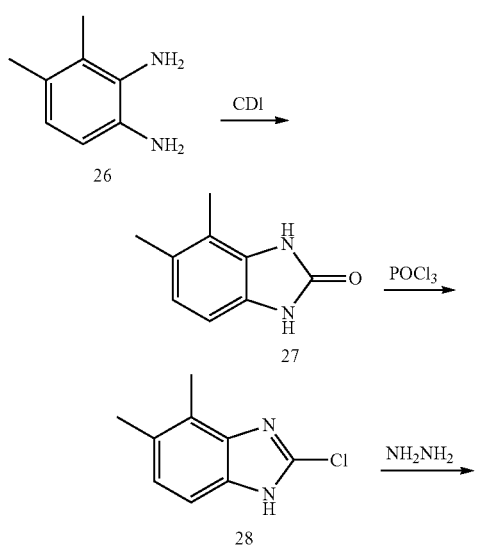

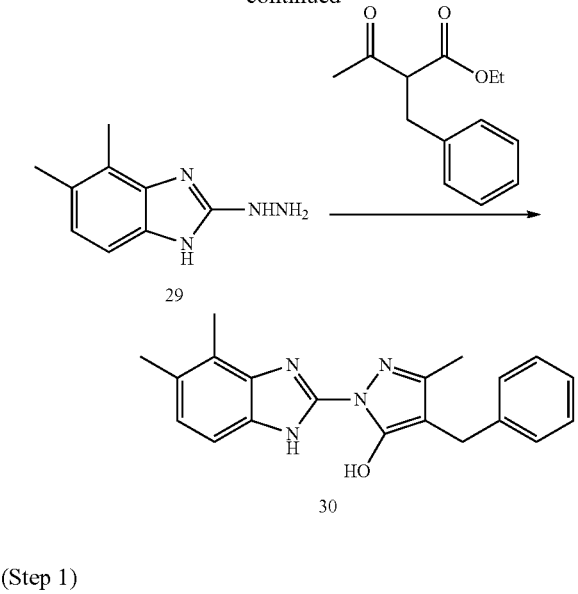

(Step 1)

Synthesis of 4,5-dimethyl-1,3-dihydrobenzimidazol-2-one (27)

Using 4,5-dimethyl-1,2-phenylenediamine (26) and by a method similar to that in Example 1, step 1, 4,5-dimethyl-1,3-dihydrobenzimidazol-2-one (27) was obtained.

ESI-HRMS (positive ion, sodium formate): calcd for C$_9$H$_{11}$N$_2$O([M+H]$^+$) 163.0866. found 163.0850

NMR (DMSO-d$_5$, δ): 2.16 (3H, s), 2.18 (3H, s), 6.63 (1H, d, J=7.8 Hz), 6.72 (1H, d, J=7.8 Hz), 10.40 (1H, s), 10.55 (1H, s)
(Step 2)

Synthesis of 2-chloro-4,5-dimethyl-1H-benzimidazole (28)

Using 4,5-dimethyl-1,3-dihydrobenzimidazol-2-one (27) and by a method similar to that in Example 1, step 2, 2-chloro-4,5-dimethyl-1H-benzimidazole (28) was obtained.

NMR (DMSO-d$_6$, δ): 2.30 (3H, s), 2.37 (3H, s), 7.02 (1H, d, J=8.2 Hz), 7.20 (1H, d, J=8.2 Hz)
(Step 3)

Synthesis of 2-hydrazino-4,5-dimethyl-1H-benzimidazole (29)

Using 2-chloro-4,5-dimethyl-1H-benzimidazole (28) and by a method similar to that in Example 1, step 3, 2-hydrazino-4,5-dimethyl-1H-benzimidazole (29) was obtained.

ESI-HRMS (positive ion, sodium formate): calcd for C$_9$H$_{13}$N$_4$([M+H]$^+$) 177.1135. found 177.1169

NMR (DMSO-d$_6$, δ): 2.22 (3H, s), 2.28 (3H, s), 4.36 (2H, br s), 6.56-6.73 (1H, m), 6.81 (1H, d, J=7.8 Hz), 7.61 (1H, br s), 10.80 (1H, br s)
(Step 4)

Synthesis of 1-(4,5-dimethyl-1H-benzimidazol-2-yl)-3-methyl-4-(phenylmethyl)-1H-pyrazol-5-ol (30)

Using 2-hydrazino-4,5-dimethyl-1H-benzimidazole (29) and in the same manner as in Example 1, step 4, 1-(4,5-dimethyl-1H-benzimidazol-2-yl)-3-methyl-4-(phenylmethyl)-1H-pyrazol-5-ol (30) was obtained.

ESI-HRMS (positive ion, sodium formate): calcd for $C_{20}H_{21}N_4O([M+H]^+)$ 333.1710. found 333.1726
NMR (DMSO-$d_6$, δ): 2.17 (3H, s), 2.31 (3H, s), 2.44 (3H, s), 3.61 (2H, s), 6.96 (1H, d, J=7.8 Hz), 7.12-7.30 (6H, m)
IR(KBr): 3026, 2920, 2866, 1677, 1600 cm$^{-1}$
HPLC retention time: 12.1 min Example 7

Synthesis of 4-[(4-chlorophenyl)methyl]-3-methyl-1-(5-methyl-1H-benzimidazol-2-yl)-1H-pyrazol-5-ol (32)

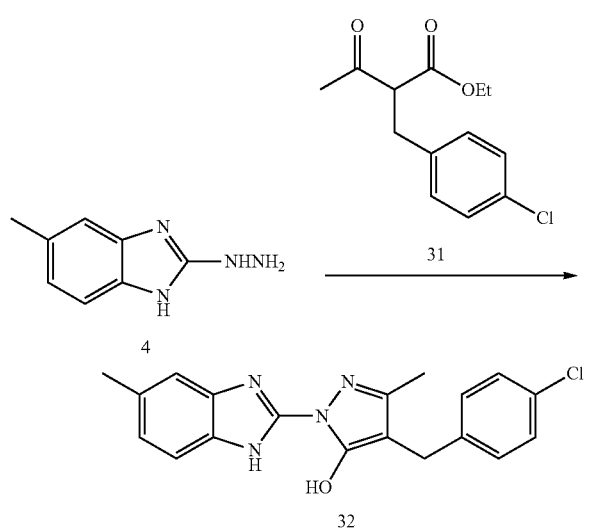

(Step 1)

Synthesis of ethyl 2-acetyl-3-(4-chlorophenyl)propanoate (31)

Using 4-chlorobenzylbromide and in the same manner as in Example 9, step 1, ethyl 2-acetyl-3-(4-chlorophenyl)propanoate (31) was obtained.
ESI-HRMS (positive ion, sodium formate): calcd for $C_{13}H_{15}ClO_3Na([M+Na]^+)$ 277.0602. found 277.0594
NMR (CDCl$_3$, δ): 1.19-1.24 (3H, m), 2.20 (3H, s), 3.06-3.18 (2H, m), 3.70-3.76 (1H, m), 4.09-4.21 (2H, m), 7.09-7.14 (2H, m), 7.21-7.26 (2H, m)

(Step 2)

Synthesis of 4-[(4-chlorophenyl)methyl]-3-methyl-1-(5-methyl-1H-benzimidazol-2-yl)-1H-pyrazol-5-ol (32)

Using 2-hydrazino-5-methyl-1H-benzimidazole (4) obtained in Example 1, step 3 and ethyl 2-acetyl-3-(4-chlorophenyl)propanoate (31), and by a method similar to that in Example 1, step 4, 4-[(4-chlorophenyl)methyl]-3-methyl-1-(5-methyl-1H-benzimidazol-2-yl)-1H-pyrazol-5-ol (32) was obtained.
ESI-HRMS (positive ion, sodium formate): calcd for $C_{19}H_{18}ClN_4O([M+H]^+)$ 353.1164. found 353.1151
NMR (DMSO-$d_6$, δ): 2.15 (3H, s), 2.39 (3H, s), 3.58 (2H, s), 6.98 (1H, dd, J=0.9 and 8.2 Hz), 7.27-7.35 (5H, m), 7.39 (1H, d, J=8.2 Hz)
IR(KBr): 3032, 2921, 2864, 1665, 1552 cm$^{-1}$
HPLC retention time: 12.0 min Example 8

Synthesis of 3-methyl-1-(5-methyl-1H-benzimidazol-2-yl)-4-[(4-phenylphenyl)methyl]-1H-pyrazol-5-ol (34)

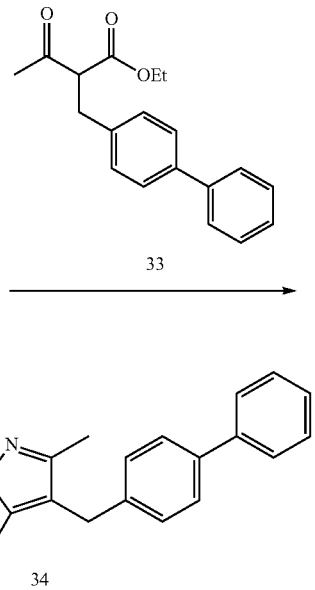

(Step 1)

Synthesis of ethyl 2-acetyl-3-(4-phenylphenyl)propanoate (33)

Using 4-phenylbenzylbromide and in the same manner as in Example 9, step 1, ethyl 2-acetyl-3-(4-phenylphenyl)propanoate (33) was obtained.
ESI-HRMS (positive ion, sodium formate): calcd for $C_{19}H_{20}O_3Na([M+Na]^+)$ 319.1310. found 319.1336
NMR (CDCl$_3$, δ): 1.22 (3H, t, J=7.3 Hz), 2.22 (3H, s), 3.15-3.25 (2H, m), 3.78-3.84 (1H, m), 4.10-4.23 (2H, m), 7.23-7.27 (2H, m), 7.30-7.35 (1H, m), 7.39-7.45 (2H, m), 7.48-7.53 (2H, m), 7.54-7.58 (2H, m)

(Step 2)

Synthesis of 3-methyl-1-(5-methyl-1H-benzimidazol-2-yl)-4-[(4-phenylphenyl)methyl]-1H-pyrazol-5-ol (34)

Using 2-hydrazino-5-methyl-1H-benzimidazole (4) obtained in Example 1, step 3 and ethyl 2-acetyl-3-(4-phenylphenyl)propanoate (33), and by a method similar to that in Example 1, step 4, 3-methyl-1-(5-methyl-1H-benzimidazol-2-yl)-4-[(4-phenylphenyl)methyl]-1H-pyrazol-5-ol (34) was obtained.
ESI-HRMS (positive ion, sodium formate): calcd for $C_{25}H_{23}N_4O([M+H]^+)$ 395.1866. found 395.1834
NMR (DMSO-$d_6$, δ): 2.19 (3H, s), 2.39 (3H, s), 3.63 (2H, s), 6.96-7.00 (1H, m), 7.30-7.47 (7H, m), 7.54-7.64 (4H, m)
IR(KBr): 3246, 3031, 2922, 2864, 1656, 1557, 1541 cm$^{-1}$
HPLC retention time: 12.7 min

Example 9

Synthesis of 4-[(3,4-dichlorophenyl)methyl]-3-methyl-1-(5-methyl-1H-benzimidazol-2-yl)-1H-pyrazol-5-ol (36)

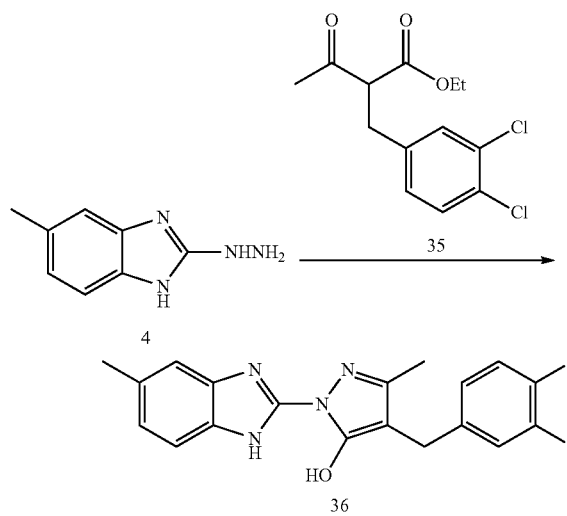

(Step 1)

Synthesis of ethyl 2-acetyl-3-(3,4-dichlorophenyl)propanoate (35)

To a solution of ethyl acetoacetate (1.0 g) in tetrahydrofuran (20 mL) was added sodium hydride (about 60% oil suspension) (0.37 g) in several portions under ice-cooling under a nitrogen atmosphere. After stirring at room temperature for 1 hr, 3,4-dichlorobenzylbromide (1.4 mL) was added to the reaction mixture. After stirring at room temperature for 2 hr, the reaction mixture was poured into a mixture of ethyl acetate and water. The organic phase was washed successively with water and brine, and dried over magnesium sulfate. The solvent was evaporated under reduced pressure, and the residue was purified by column chromatography on silica gel by eluting with toluene. An eluted fraction containing the desired product was recovered and evaporated under reduced pressure to give ethyl 2-acetyl-3-(3,4-dichlorophenyl)propanoate (35) (1.6 g).

ESI-HRMS (positive ion, sodium formate): calcd for $C^{13}H_{14}Cl_2O_3Na([M+Na]^+)$ 311.0212. found 311.0203

NMR (CDCl$_3$, δ): 1.19-1.25 (3H, m), 2.23 (3H, s), 3.04-3.16 (2H, m), 3.69-3.75 (1H, m), 4.11-4.23 (2H, m), 6.97-7.05 (1H, m), 7.22-7.36 (2H, m)

(Step 2)

Synthesis of 4-[(3,4-dichlorophenyl)methyl]-3-methyl-1-(5-methyl-1H-benzimidazol-2-yl)-1H-pyrazol-5-ol (36)

Using 2-hydrazino-5-methyl-1H-benzimidazole (4) obtained in Example 1, step 3 and ethyl 2-acetyl-3-(3,4-dichlorophenyl)propanoate (35), and by a method similar to that in Example 1, step 4, 4-[(3,4-dichlorophenyl)methyl]-3-methyl-1-(5-methyl-1H-benzimidazol-2-yl)-1H-pyrazol-5-ol (36) was obtained.

ESI-HRMS (positive ion, sodium formate): calcd for $C_{19}H_{16}Cl_2N_4O([M+H]^+)$ 387.0779. found 387.0748

NMR (DMSO-d$_6$, δ): 2.17 (3H, s), 2.39 (3H, s), 3.60 (2H, s), 6.98 (1H, dd, J=0.9 and 8.2 Hz), 7.27 (1H, dd, J=1.8 and 8.2 Hz), 7.32 (1H, br s), 7.39 (1H, d, J=8.2 Hz), 7.52 (1H, d, J=8.2 Hz), 7.55 (1H, d, J=1.8 Hz)

IR(KBr): 3050, 2922, 2865, 1665, 1561 cm$^{-1}$

HPLC retention time: 12.7 min

Example 10

Synthesis of 3-methyl-1-(5-methyl-1H-benzimidazol-2-yl)-4-[(4-trifluorophenyl)methyl]-1H-pyrazol-5-ol (38)

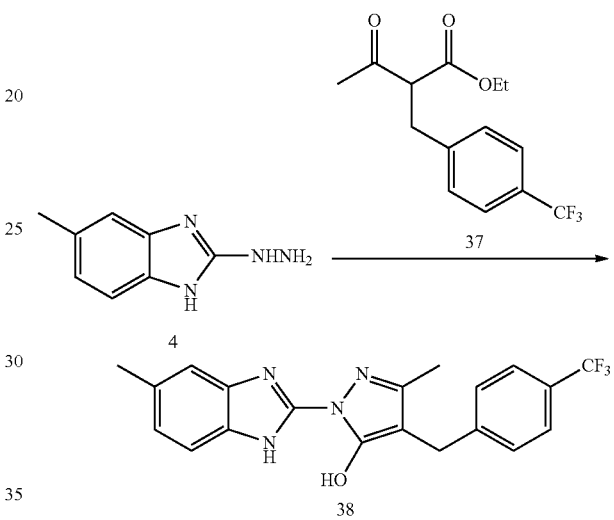

(Step 1)

Synthesis of ethyl 2-acetyl-3-(4-trifluorophenyl)propanoate (37)

Using 4-trifluorobenzylbromide and in the same manner as in Example 9, step 1, ethyl 2-acetyl-3-(4-trifluorophenyl)propanoate (37) was obtained.

ESI-HRMS (positive ion, sodium formate): calcd for $C_{13}H_{15}F_3O_3Na([M+Na]_+)$ 311.0866. found 311.0878

NMR (CDC$_3$, δ): 1.21 (3H, t, J=7.1 Hz), 2.22 (3H, s), 3.15-3.27 (2H, m), 3.74-3.80 (1H, m), 4.10-4.22 (2H, m), 7.28-7.32 (2H, m), 7.51-7.55 (2H, m)

(Step 2)

Synthesis of 3-methyl-1-(5-methyl-1H-benzimidazol-2-yl)-4-[(4-trifluorophenyl)methyl]-1H-pyrazol-5-ol (38)

Using 2-hydrazino-5-methyl-1H-benzimidazole (4) obtained in Example 1, step 3 and ethyl 2-acetyl-3-(4-trifluorophenyl)propanoate (37), and by a method similar to that in Example 1, step 4, 3-methyl-1-(5-methyl-1H-benzimidazol-2-yl)-4-[(4-trifluorophenyl)methyl]-1H-pyrazol-5-ol (38) was obtained.

ESI-HRMS (positive ion, sodium formate): calcd for $C_{20}H_{18}F_3N_4O([M+H]^+)$ 387.1433. found 387.1414

NMR (DMSO-d$_6$, δ): 2.17 (3H, s), 2.39 (3H, s), 3.69 (2H, s), 6.99 (1H, dd, J=0.9 and 8.2 Hz), 7.32 (1H, br s), 7.39 (1H, d, J=8.2 Hz), 7.50 (2H, d, J=8.2 Hz), 7.64 (2H, d, J=8.2 Hz)

IR(KBr): 3268, 2923, 2865, 1666, 1552 cm$^{-1}$
HPLC retention time: 12.4 min

Example 11

Synthesis of 3-methyl-1-(5-methyl-1H-benzimidazol-2-yl)-4-(2-naphthylmethyl)-1H-pyrazol-5-ol (40)

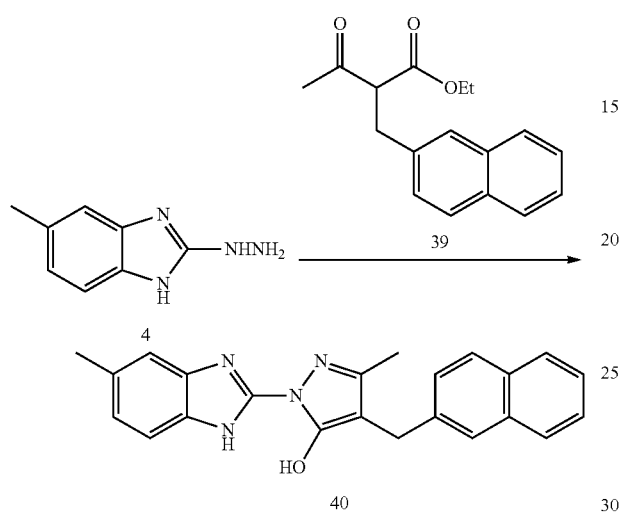

(Step 1)

Synthesis of ethyl 2-acetyl-3-(2-naphthyl)propanoate (39)

Using naphthylmethylbromide and in the same manner as in Example 9, step 1, ethyl 2-acetyl-3-(2-naphthyl)propanoate (39) was obtained.

ESI-HRMS (positive ion, sodium formate): calcd for $C_{17}H_{18}O_3Na([M+Na]^+)$ 293.1148. found 293.1141

NMR (CDC$_3$, δ): 1.13-1.21 (3H, m), 2.20 (3H, s), 3.27-3.38 (2H, m), 3.88 (1H, t, J=7.8 Hz), 4.08-4.21 (2H, m), 7.28-7.34 (1H, m), 7.40-7.48 (2H, m), 7.63 (1H, s), 7.72-7.82 (3H, m)

(Step 2)

Synthesis of 3-methyl-1-(5-methyl-1H-benzimidazol-2-yl)-4-(2-naphthylmethyl)-1H-pyrazol-5-ol (40)

Using 2-hydrazino-5-methyl-1H-benzimidazole (4) obtained in Example 1, step 3 and ethyl 2-acetyl-3-(2-naphthyl)propanoate (39), and by a method similar to that in Example 1, step 4, 3-methyl-1-(5-methyl-1H-benzimidazol-2-yl)-4-(2-naphthylmethyl)-1H-pyrazol-5-ol (40) was obtained.

ESI-HRMS (positive ion, sodium formate): calcd for $C_{23}H_{20}N_4ONa([M+Na]^+)$ 391.1529. found 391.1516

NMR (DMSO-d$_6$, δ): 2.19 (3H, s), 2.39 (3H, s), 3.77 (2H, s), 6.98 (1H, d, J=7.8 Hz), 7.32 (1H, br s), 7.37-7.50 (4H, m), 7.74 (1H, br s), 7.78-7.88 (3H, m)

IR(KBr): 3331, 3057, 2982, 2922, 1636, 1558 cm$^{-1}$
HPLC retention time: 12.2 min Example 12

Synthesis of 4-[[(1,1-dimethylethyl)phenyl]methyl]-3-methyl-1-(5-methyl-1H-benzimidazol-2-yl)-1H-pyrazol-5-ol (42)

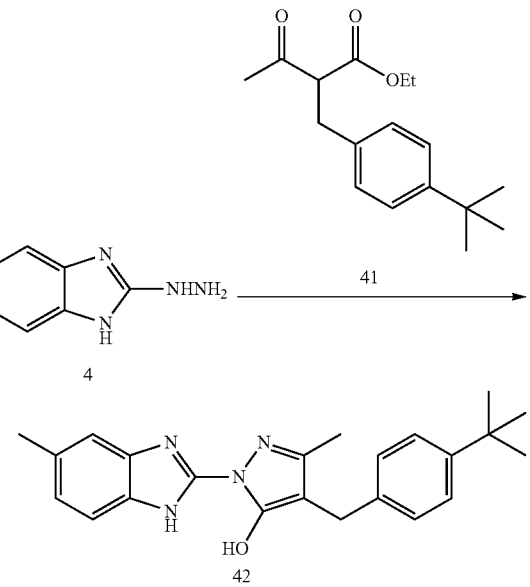

(Step 1)

Synthesis of ethyl 2-acetyl-3-[(1,1-dimethylethyl)phenyl]propanoate (41)

Using 4-1,1-dimethylethylbenzylbromide and in the same manner as in Example 9, step 1, ethyl 2-acetyl-3-[(1,1-dimethylethyl)phenyl]propanoate (41) was obtained.

ESI-HRMS (positive ion, sodium formate): calcd for $C_{17}H_{24}O_3Na([M+Na]^+)$ 299.1617. found 299.1628

NMR (CDC$_3$, δ): 1.19 (3H, t, J=7.3 Hz), 1.28 (9H, s), 2.19 (3H, s), 3.13 (2H, d, J=7.3 Hz), 3.76 (1H, t, J=7.3 Hz), 4.15 (2H, q, J=7.3 Hz), 7.07-7.13 (2H, m), 7.26-7.37 (2H, m)

(Step 2)

Synthesis of 4-[[(1,1-dimethylethyl)phenyl]methyl]-3-methyl-1-(5-methyl-1H-benzimidazol-2-yl)-1H-pyrazol-5-ol (42)

Using 2-hydrazino-5-methyl-1H-benzimidazole (4) obtained in Example 1, step 3 and ethyl 2-acetyl-3-[(1,1-dimethylethyl)phenyl]propanoate (41), and by a method similar to that in Example 1, step 4, 4-[[(1,1-dimethylethyl)phenyl]methyl]-3-methyl-1-(5-methyl-1H-benzimidazol-2-yl)-1H-pyrazol-5-ol (42) was obtained.

ESI-HRMS (positive ion, sodium formate): calcd for $C_{23}H_{26}N_4O([M+H]^+)$ 375.2179. found 375.2184

NMR (DMSO-d$_6$, δ): 1.24 (9H, s), 2.16 (3H, s), 2.39 (3H, s), 3.54 (2H, s), 6.98 (1H, dd, J=0.9 and 8.2 Hz), 7.17-7.21 (2H, m), 7.25-7.29 (2H, m), 7.31 (1H, br s), 7.39 (1H, d, J=8.2 Hz)

IR(KBr): 3233, 3024, 2961, 2865, 1658, 1558 cm$^{-1}$
HPLC retention time: 13.1 min Using the corresponding starting compounds and in the same manner as in Example 1, the compounds of Examples 13-48 were synthesized. The following Tables summarize the structures of Examples 1-48 and physicochemical properties thereof.

TABLE 1

| Ex. No. | Structure | 1H-NMR | IR | ESI-HRMS | HPLC retention time (min) | purity (%) |
|---|---|---|---|---|---|---|
| 1 | 5-Me-benzimidazole-pyrazole(Me, OH, CH2Ph) | NMR (DMSO-d6, δ): 2.15 (3H, s), 2.39 (3H, s), 3.59 (2H, s), 6.96-7.00 (1H, m), 7.13-7.20 (1H, m), 7.23-7.29 (4H, m), 7.31 (1H, br s), 7.39 (1H, d, J = 8.2 Hz) | IR (KBr): 3312, 3024, 2936, 2915, 1653, 1553 cm$^{-1}$ | ESI-HRMS (positive ion, sodium formate) calcd for C$_{18}$H$_{18}$N$_4$O ([M + H]$^+$) 319.1559; found 319.1588 | 11.2 | 99.4 |
| 2 | 4-Me-benzimidazole-pyrazole(Me, OH, CH2Ph) | NMR (DMSO-d6, δ): 2.18 (3H, s), 2.52 (3H, s), 3.61 (2H, s), 6.95-6.99 (1H, m), 7.05 (1H, t, J = 7.8 Hz), 7.13-7.21 (1H, m), 7.22-7.30 (4H, m), 7.35 (1H, d, J = 7.8 Hz) | IR (KBr): 3272, 3027, 1667, 1628, 1575 cm$^{-1}$ | ESI-HRMS (positive ion, sodium formate) calcd for C$_{18}$H$_{18}$N$_4$O ([M + H]$^+$) 319.1559; found 319.1562 | 11.9 | 98.6 |
| 3 | 5-Cl-benzimidazole-pyrazole(Me, OH, CH2Ph) | NMR (DMSO-d6, δ): 2.17 (3H, s), 3.59 (2H, s), 7.13-7.21 (2H, m), 7.24-7.30 (4H, m), 7.52 (1H, d, J = 8.7 Hz), 7.55 (1H, d, J = 2.3 Hz) | IR (KBr): 3263, 3031, 2914, 2842, 1654, 1623, 1556 cm$^{-1}$ | ESI-HRMS (positive ion, sodium formate) calcd for C$_{18}$H$_{15}$ClN$_4$O ([M + H]$^+$) 339.1007; found 339.0978 | 13.1 | 98.9 |
| 4 | 5-CF3-benzimidazole-pyrazole(Me, OH, CH2Ph) | NMR (DMSO-d6, δ): 2.19 (3H, s), 3.60 (2H, s), 7.14-7.21 (1H, m), 7.24-7.31 (4H, m), 7.46-7.52 (1H, m), 7.70 (1H, d, J = 8.2 Hz), 7.84 (1H, s) | IR (KBr): 3033, 2935, 2901, 1637, 1551 cm$^{-1}$ | ESI-HRMS (positive ion, sodium formate) calcd for C$_{19}$H$_{16}$F$_3$N$_4$O ([M + H]$^+$) 373.1271; found 373.1259 | 13.6 | 98.8 |
| 5 | 5-tBu-benzimidazole-pyrazole(Me, OH, CH2Ph) | NMR (DMSO-d6, δ): 1.33 (9H, s), 2.15 (3H, s), 3.59 (2H, s), 7.13-7.20 (1H, m), 7.22-7.30 (5H, m), 7.43 (1H, d, J = 8.2 Hz), 7.51 (1H, br s) | IR (KBr): 3026, 2961, 2903, 1655, 1558 cm$^{-1}$ | ESI-HRMS (positive ion, sodium formate) calcd for C$_{22}$H$_{25}$N$_4$O ([M + H]$^+$) 361.2023; found 361.2029 | 12.5 | 97.9 |
| 6 | 4,5-diMe-benzimidazole-pyrazole(Me, OH, CH2Ph) | NMR (DMSO-d6, δ): 2.17 (3H, s), 2.31 (3H, s), 2.44 (3H, s), 3.61 (2H, s), 6.96 (1H, d, J = 7.8 Hz), 7.12-7.30 (6H, m) | IR (KBr): 3026, 2920, 2866, 1677, 1600 cm$^{-1}$ | ESI HRMS (positive ion, sodium formate) calcd for C$_{20}$H$_{21}$N$_4$O ([M + H]$^+$) 333.1710; found 333.1726 | 12.1 | 97.4 |
| 7 | 5-Me-benzimidazole-pyrazole(Me, OH, CH2-4-Cl-Ph) | NMR (DMSO-d6, δ): 2.15 (3H, s), 2.39 (3H, s), 3.58 (2H, s), 6.98 (1H, dd, J = 0.9 and 8.2 Hz), 7.27-7.35 (5H, m), 7.39 (1H, d, J = 8.2 Hz) | IR (KBr): 3032, 2921, 2864, 1665, 1552 cm$^{-1}$ | ESI HRMS (positive ion, sodium formate) calcd for C$_{18}$H$_{18}$ClN$_4$O ([M + H]$^+$) 353.1164; found 353.1151 | 12.0 | 98.1 |
| 8 | 5-Me-benzimidazole-pyrazole(Me, OH, CH2-4-biphenyl) | NMR (DMSO-d6, δ): 2.19 (3H, s), 2.39 (3H, s), 3.63 (2H, s), 6.96-7.00 (1H, m), 7.30-7.47 (7H, m), 7.54-7.64 (4H, m) | IR (KBr): 3246, 3031, 2922, 2864, 1656, 1557, 1541 cm$^{-1}$ | ESI HRMS (positive ion, sodium formate) calcd for C$_{25}$H$_{23}$N$_4$O ([M + H]$^+$) 395.1866; found 395.1834 | 12.7 | 98.3 |

TABLE 1-continued

| Ex. No. | Structure | 1H-NMR | IR | ESI-HRMS | HPLC retention time (min) | purity (%) |
|---|---|---|---|---|---|---|
| 9 | (benzimidazole-Me / pyrazole-Me / CH2-3,4-dichlorophenyl / OH) | NMR (DMSO-d$_6$, δ): 2.17 (3H, s), 2.39 (3H, s), 3.60 (2H, s), 6.98 (1H, dd, J = 0.9 and 8.2 Hz), 7.27 (1H, dd, J = 1.8 and 8.2 Hz), 7.32 (1H, br s), 7.39 (1H, d, J = 8.2 Hz), 7.52 (1H, d, J = 8.2 Hz), 7.55 (1H, d, J = 1.8 Hz) | IR (KBr): 3050, 2922, 2865 1665, 1561 cm$^{-1}$ | ESI-HRMS (positive ion, sodium formate) calcd for C$_{19}$H$_{16}$Cl$_2$N$_4$O ([M + H]$^+$) 387.0779; found 387.0748 | 12.7 | 97.8 |
| 10 | (benzimidazole-Me / pyrazole-Me / CH2-4-CF3-phenyl / OH) | NMR (DMSO-d$_6$, δ): 2.17 (3H, s), 2.39 (3H, s), 3.69 (2H, s), 6.99 (1H, dd, J = 0.9 and 8.2 Hz), 7.32 (1H, br s), 7.39 (1H, d, J = 8.2 Hz), 7.50 (2H, d, J = 8.2 Hz), 7.64 (2H, d, J = 8.2 Hz) | IR (KBr): 3268, 2923, 2865, 1666, 1552 cm$^{-1}$ | ESI-HRMS (positive ion, sodium formate) calcd for C$_{20}$H$_{18}$F$_3$N$_4$O ([M + H]$^+$) 387.1433; found 387.1414 | 12.4 | 99.0 |
| 11 | (benzimidazole-Me / pyrazole-Me / CH2-2-naphthyl / OH) | NMR (DMSO-d$_6$, δ): 2.19 (3H, s), 2.39 (3H, s), 3.77 (2H, s), 6.98 (1H, d, J = 7.8 Hz), 7.32 (1H, br s), 7.37-7.50 (4H, m), 7.74 (1H, br s), 7.78-7.88 (3H, m) | IR (KBr): 3331, 3057, 2982, 2919, 1636, 1558 cm$^{-1}$ | ESI-HRMS (positive ion, sodium formate) calcd for C$_{23}$H$_{20}$N$_4$ONa ([M + H]$^+$) 391.1529; found 391.1516 | 12.2 | 99.0 |
| 12 | (benzimidazole-Me / pyrazole-Me / CH2-4-tBu-phenyl / OH) | NMR (DMSO-d$_6$, δ): 1.24 (9H, s), 2.16 (3H, s), 2.39 (3H, s), 3.54 (2H, s), 6.98 (1H, dd, J = 0.9 and 8.2 Hz), 7.17-7.21 (2H, m), 7.25-7.29 (2H, m), 7.31 (1H, br s), 7.39 (1H, d, J = 8.2 Hz) | IR (KBr): 3233, 3024, 2961, 2865, 1658, 1558 cm$^{-1}$ | ESI-HRMS (positive ion, sodium formate) calcd for C$_{23}$H$_{25}$N$_4$O ([M + H]$^+$) 375.2179; found 375.2184 | 13.1 | 98.4 |
| 13 | (benzimidazole / pyrazole-3,4-diMe / OH) | NMR (DMSO-d$_6$, δ): 1.77 (3H, s), 2.17 (3H, s), 7.12-7.18 (2H, m), 7.50-7.65 (2H, m) | IR (KBr): 3296, 3049, 2921, 2862, 1628, 1547 cm$^{-1}$ | ESI-HRMS (positive ion, sodium formate) calcd for C$_{12}$H$_{13}$N$_4$O ([M + H]$^+$) 229.1084; found 229.1091 | 8.5 | 98.3 |
| 14 | (benzimidazole / pyrazole-Me / CH2-phenyl / OH) | NMR (DMSO-d$_6$, δ): 2.17 (3H, s), 3.60 (2H, s), 7.13-7.19 (3H, m), 7.24-7.30 (4H, m), 7.49-7.55 (2H, m) | IR (KBr): 3269, 3026, 1627, 1542 cm$^{-1}$ | ESI-HRMS (positive ion, sodium formate) calcd for C$_{18}$H$_{17}$N$_4$O ([M + H]$^+$) 305.1397; found 305.1396 | 11.0 | 99.0 |
| 15 | (benzimidazole / pyrazole-Me / OH) | NMR (DMSO-d$_6$, δ): 2.20 (3H, s), 5.24 (1H, s), 7.14-7.20 (2H, m), 7.49-7.55 (2H, m) | IR (KBr): 3310, 3043, 2905, 1626, 1559 cm$^{-1}$ | ESI-HRMS (positive ion, sodium formate) calcd for C$_{11}$H$_{11}$N$_4$O ([M + H]$^+$) 215.0927; found 215.0933 | 7.3 | 98.6 |
| 16 | (benzimidazole / pyrazole-Me / CH2-3,4-dichlorophenyl / OH) | NMR (DMSO-d$_6$, δ): 2.19 (3H, s), 3.61 (2H, s), 7.14-7.19 (2H, m), 7.28 (1H, dd, J = 1.8 and 8.2 Hz), 7.50-7.57 (4H, m) | IR (KBr): 3183, 2890, 1626, 1606 cm$^{-1}$ | ESI-HRMS (positive ion, sodium formate) calcd for C$_{18}$H$_{15}$Cl$_2$N$_4$O ([M + H]$^+$) 373.0617; found 373.0621 | 12.6 | 99.1 |
| 17 | (benzimidazole-Me / pyrazole-3,4-diMe / OH) | NMR (DMSO-d$_6$, δ): 1.77 (3H, s), 2.16 (3H, s), 2.39 (3H, s), 6.98 (1H, dd, J = 0.9, 8.2 Hz), 7.32 (1H, br s), 7.40 (1H, d, J = 8.2 Hz) | IR (KBr): 3308, 3018, 2920, 2861, 1635, 1573 cm$^{-1}$ | ESI-HRMS (positive ion, sodium formate) calcd for C$_{13}$H$_{15}$N$_4$O ([M + H]$^+$) 243.1240; found 243.1259 | 9.0 | 98.9 |

TABLE 1-continued

| Ex. No. | Structure | 1H-NMR | IR | ESI-HRMS | HPLC retention time (min) | purity (%) |
|---|---|---|---|---|---|---|
| 18 | (benzimidazole-pyrazole with Me, OH, Ph) | NMR (DMSO-d$_6$, δ): 2.39 (3H, s), 7.14-7.26 (3H, m), 7.34-7.40 (2H, m), 7.54-7.59 (2H, m), 7.63-7.67 (2H, m) | IR (KBr): 3056, 2984, 1665, 1596, 1514 cm$^{-1}$ | ESI-HRMS (positive ion, sodium formate) calcd for C$_{17}$H$_{15}$N$_4$O ([M + H]$^+$) 291.1240; found 291.1253 | 11.4 | 99.1 |
| 19 | (benzimidazole-pyrazole with Me, OH, CH$_2$-naphthyl) | NMR (DMSO-d$_6$, δ): 2.19 (3H, s), 3.77 (2H, s), 7.13-7.18 (2H, m), 7.40-7.55 (5H, m), 7.73 (1H, br s), 7.80-7.86 (3H, m) | IR (KBr): 3068, 2923, 1643, 1596, 1528 cm$^{-1}$ | ESI-HRMS (positive ion, sodium formate) calcd for C$_{22}$H$_{18}$N$_4$O ([M + H]$^+$) 355.1553; found 355.1577 | 12.1 | 99.1 |
| 20 | (benzimidazole-pyrazole with Me, OH, CH$_2$COOMe) | NMR (MeOH-d$_4$, δ): 2.23 (3H, s), 3.39 (2H, s), 3.70 (3H, s), 7.23-7.29 (2H, m), 7.51-7.56 (2H, m) | IR (KBr): 2997, 2950, 1734, 1690, 1606, 1500 cm$^{-1}$ | ESI-HRMS (positive ion, sodium formate) calcd for C$_{14}$H$_{15}$N$_4$O$_3$ ([M + H]$^+$) 287.1139; found 287.1145 | 8.7 | 97.5 |
| 21 | (benzimidazole-pyrazole with Me, OH, CH$_2$COOH) | NMR (DMSO-d$_6$, δ): 2.15 (3H, s), 3.22 (2H, m), 7.13-7.18 (2H, m), 7.49-7.55 (2H, m) | IR (KBr): 3433, 2993, 1690, 1609, 1525 cm$^{-1}$ | ESI-HRMS (positive ion, sodium formate) calcd for C$_{13}$H$_{13}$N$_4$O$_3$ ([M + H]$^+$) 273.0982; found 273.0967 | 7.9 | 97.0 |
| 22 | (methylbenzimidazole-pyrazole with Me, Me, OH) | NMR (DMSO-d$_6$, δ): 1.78 (3H, s), 2.15 (3H, s), 2.52 (3H, s), 6.94-6.98 (1H, m), 7.05 (1H, t, J = 7.8 Hz), 7.35 (1H, d, 7.8 Hz) | IR (KBr): 3243, 2912, 1672, 1606, 1497 cm$^{-1}$ | ESI-HRMS (positive ion, sodium formate) calcd for C$_{13}$H$_{14}$N$_4$ONa ([M + Na]$^+$) 265.1060; found 265.1062 | 9.2 | 98.3 |
| 23 | (benzimidazole-pyrazole with Me, OH, CH$_2$-2-chlorophenyl) | NMR (DMSO-d$_6$, δ): 2.16 (3H, s), 3.69 (2H, s), 7.13-7.19 (2H, m), 7.20-7.29 (2H, m), 7.32-7.36 (1H, m), 7.41-7.44 (1H, m), 7.50-7.55 (2H, m) | IR (KBr): 3280, 2900, 1866, 1619, 1573 cm$^{-1}$ | ESI HRMS (positive ion, sodium formate) calcd for C$_{16}$H$_{16}$ClN$_4$O ([M + H]$^+$) 339.1007; found 339.1022 | 11.8 | 98.5 |
| 24 | (benzimidazole-pyrazole with Me, OH, CH$_2$-4-CF$_3$-phenyl) | NMR (DMSO-d$_6$, δ): 2.18 (3H, s), 3.69 (2H, s), 7.12-7.18 (2H, m), 7.47-7.54 (4H, m), 7.63 (2H, d, J = 8.2 Hz) | IR (KBr): 3263, 2917, 1667, 1620, 1548 cm$^{-1}$ | ESI-HRMS (positive ion, sodium formate) calcd for C$_{19}$H$_{16}$F$_3$N$_4$O ([M + H]$^+$) 373.1270; found 373.1287 | 12.2 | 98.9 |
| 25 | (benzimidazole-pyrazole with Me, OH, CH$_2$-4-F-phenyl) | NMR (DMSO-d$_6$, δ): 2.17 (3H, s), 3.59 (2H, s), 7.06-7.11 (2H, m), 7.14-7.18 (2H, m), 7.29-7.33 (2H, m), 7.51-7.54 (2H, m) | IR (KBr): 3246, 3069, 2910, 1657, 1605, 1507 cm$^{-1}$ | ESI-HRMS (positive ion, sodium formate) calcd for C$_{18}$H$_{15}$FN$_4$ONa ([M + Na]$^+$) 345.1122; found 345.1114 | 11.2 | 97.5 |
| 26 | (benzimidazole-pyrazole with Me, OH, CH$_2$-4-tBu-phenyl) | NMR (DMSO-d$_6$, δ): 1.25 (9H, s), 2.17 (3H, s), 3.55 (2H, s), 7.13-7.22 (4H, m), 7.26-7.30 (2H, m), 7.49-7.55 (2H, m) | IR (KBr): 3306, 3058, 2961, 1643, 1553 cm$^{-1}$ | ESI-HRMS (positive ion, sodium formate) calcd for C$_{22}$H$_{25}$N$_4$O ([M + H]$^+$) 361.2022; found 361.2022 | 13.0 | 98.7 |

TABLE 1-continued

| Ex. No. | Structure | 1H-NMR | IR | ESI-HRMS | HPLC retention time (min) | purity (%) |
|---|---|---|---|---|---|---|
| 27 | benzimidazole-pyrazole(Me,OH)-CH2-(3-Cl-phenyl) | NMR (DMSO-$d_6$, δ): 2.19 (3H, s), 3.61 (2H, s), 7.13-7.19 (2H, m), 7.21-7.37 (4H, m), 7.50-7.55 (2H, m) | IR (KBr): 3350, 3068, 2919, 1629, 1553 cm$^{-1}$ | ESI-HRMS (positive ion, sodium formate) calcd for $C_{18}H_{16}ClN_4O$ ([M + H]$^+$) 339.1007; found 339.1006 | 11.8 | 97.9 |
| 28 | benzimidazole-pyrazole(Me,OH)-CH2-(2,4-diCl-phenyl) | NMR (DMSO-$d_6$, δ): 2.16 (3H, s), 3.66 (2H, s), 7.14-7.19 (2H, m), 7.34-7.37 (2H, m), 7.50-7.55 (2H, m), 7.57-7.59 (1H, m) | IR (KBr): 3208, 3067, 2916, 2897, 1628, 1552 cm$^{-1}$ | ESI-HRMS (positive ion, sodium formate) calcd for $C_{18}H_{15}Cl_2N_4O$ ([M + H]$^+$) 373.0617; found 373.0630 | 12.9 | 98.1 |
| 29 | benzimidazole-pyrazole(Me,OH)-CH2-biphenyl | NMR (DMSO-$d_6$, δ): 2.20 (3H, s), 3.64 (2H, s), 7.12-7.19 (2H, m), 7.30-7.40 (3H, m), 7.41-7.47 (2H, m), 7.50-7.64 (6H, m) | IR (KBr): 3267, 3028, 1657, 1555 cm$^{-1}$ | ESI-HRMS (positive ion, sodium formate) calcd for $C_{24}H_{22}N_4O$ ([M + H]$^+$) 381.1710; found 361.1712 | 12.6 | 98.5 |
| 30 | benzimidazole-pyrazole(Me,OH)-CH2-(4-Cl-phenyl) | NMR (DMSO-$d_6$, δ): 2.17 (3H, s), 3.59 (2H, s), 7.13-7.19 (2H, m), 7.28-7.35 (4H, m), 7.49-7.55 (2H, m) | IR (KBr): 3269, 3027, 2935, 2909, 1556 cm$^{-1}$ | ESI-HRMS (positive ion, sodium formate) calcd for $C_{18}H_{17}ClN_4O$ ([M + H]$^+$) 339.1007; found 339.1010 | 11.9 | 98.4 |
| 31 | benzimidazole-pyrazole(Me,OH)-CH2-(4-OMe-phenyl) | NMR (DMSO-$d_6$, δ): 2.15 (3H, s), 3.53 (2H, s), 3.70 (3H, s), 6.80-6.86 (2H, m), 7.13-7.21 (4H, m), 7.50-7.55 (2H, m) | IR (KBr): 3259, 3040, 2903, 2834, 1627, 1547 cm$^{-1}$ | ESI-HRMS (positive ion, sodium formate) calcd for $C_{18}H_{18}N_4O_2$ ([M + H]$^+$) 335.1503; found 335.1493 | 10.8 | 98.2 |
| 32 | Me-benzimidazole-pyrazole(Me,OH)-CH2-(4-F-phenyl) | NMR (DMSO-$d_6$, δ): 2.16 (3H, s), 2.39 (3H, s), 3.58 (2H, s), 6.98 (1H, dd, J = 0.9 and 8.2 Hz), 7.04-7.12 (2H, m), 7.26-7.34 (3H, m), 7.39 (1H, d, J = 8.2 Hz) | IR (KBr): 3177, 3040, 2920, 1887, 1601 cm$^{-1}$ | ESI-HRMS (positive ion, sodium formate) calcd for $C_{18}H_{17}FN_4O$ ([M + H]$^+$) 337.1459; found 337.1443 | 11.4 | 98.3 |
| 33 | Me-benzimidazole-pyrazole(Me,OH)-CH2-(2-Cl-phenyl) | NMR (DMSO-$d_6$, δ): 2.14 (3H, s), 2.40 (3H, s), 3.68 (2H, s), 6.99 (1H, d, J = 8.2 Hz), 7.19-7.36 (4H, m), 7.36-7.45 (2H, m) | IR (KBr): 3191, 2924, 2893, 1674, 1626, 1604 cm$^{-1}$ | ESI-HRMS (positive ion, sodium formate) calcd for $C_{18}H_{17}ClN_4O$ ([M + H]$^+$) 353.1163; found 353.1175 | 12.0 | 98.8 |
| 34 | Me-benzimidazole-pyrazole(Me,OH)-CH2-(4-OMe-phenyl) | NMR (DMSO-$d_6$, δ): 2.14 (3H, s), 2.39 (3H, s), 3.51 (2H, s), 3.70 (3H, s), 6.81-6.85 (2H, m), 6.96-7.00 (1H, m), 7.16-7.21 (2H, m), 7.31(1H, br s), 7.39 (1H, d, J = 8.2 Hz) | IR (KBr): 2921, 2833, 1673, 1651, 1583 cm$^{-1}$ | ESI-HRMS (positive ion, sodium formate) calcd for $C_{20}H_{20}N_4O_2$ ([M + H]$^+$) 349.1659; found 349.1659 | 11.0 | 98.6 |
| 35 | (4-Cl-phenyl)-benzimidazole-pyrazole(Me,OH)-CH2-phenyl | NMR (DMSO-$d_6$, δ): 2.18 (3H, s), 3.60 (2H, s), 7.14-7.20 (1H, m), 7.24-7.31 (4H, m), 7.46 (1H, dd, J = 1.4 and 8.2 Hz), 7.49-7.54 (2H, m), 7.59 (1H, d, J = 8.2 Hz), 7.66-7.71 (2H, m), 7.76 (1H, br s) | IR (KBr): 3308, 3028, 2915, 1855, 1555 cm$^{-1}$ | ESI-HRMS (positive ion, sodium formate) calcd for $C_{24}H_{18}ClN_4O$ ([M + H]$^+$) 415.1302; found 415.1327 | 14.2 | 97.1 |

TABLE 1-continued

| Ex. No. | Structure | 1H-NMR | IR | ESI-HRMS | HPLC retention time (min) | purity (%) |
|---|---|---|---|---|---|---|
| 36 | (4-chlorophenyl-benzimidazole / pyrazole with Me, 4-chlorobenzyl, OH) | NMR (DMSO-d6, δ): 2.18 (3H, s), 3.60 (2H, s), 7.29-7.35 (4H, m), 7.46 (1H, dd, J = 1.4 and 8.2 Hz), 7.49-7.54 (2H, m), 7.59 (1H, d, J = 8.2 Hz), 7.66-7.71 (2H, m), 7.75 (1H, d, J = 1.4 Hz) | IR (KBr): 3309, 3051, 2923, 1656, 1557, 1542 cm$^{-1}$ | ESI-HRMS (positive ion, sodium formate) calcd for C$_{24}$H$_{18}$Cl$_2$N$_4$O ([M + H]$^+$) 449.0930; found 449.0925 | 14.9 | 98.9 |
| 37 | (phenyl-benzimidazole / pyrazole with Me, benzyl, OH) | NMR (DMSO-d6, δ): 2.18 (3H, s), 3.61 (2H, s), 7.14-7.20 (1H, m), 7.24-7.36 (5H, m), 7.43-7.50 (3H, m), 7.59 (1H, d, J = 8.2 Hz), 7.64-7.66 (2H, m), 7.76 (1H, br s) | IR (KBr): 3338, 3025, 2897, 1623, 1577, 1541 cm$^{-1}$ | ESI-HRMS (positive ion, sodium formate) calcd for C$_{24}$H$_{21}$N$_4$O ([M + H]$^+$) 381.1710; found 381.1716 | 13.2 | 98.4 |
| 38 | (phenyl-benzimidazole / pyrazole with Me, 4-chlorobenzyl, OH) | NMR (DMSO-d6, δ): 2.18 (3H, s), 3.60 (2H, s), 7.29-7.37 (5H, m), 7.44-7.50 (3H, m), 7.59 (1H, d, J = 8.2 Hz), 7.64-7.68 (2H, m), 7.76 (1H, br s) | IR (KBr): 3344, 3028, 2903, 1624, 1577 cm$^{-1}$ | ESI-HRMS (positive ion, sodium formate) calcd for C$_{24}$H$_{28}$ClN$_4$O ([M + H]$^+$) 415.1320; found 415.1323 | 13.9 | 97.7 |
| 39 | (4-methylphenyl-benzimidazole / pyrazole with Me, Me, OH) | NMR (DMSO-d6, δ): 1.78 (3H, s), 2.18 (3H, s), 2.35 (3H, s), 7.27 (2H, d, J = 7.8 Hz), 7.42 (1H, dd, J = 1.8, 8.2 Hz), 7.51-7.59 (3H, m), 7.73 (1H, br s) | IR (KBr): 3291, 3023, 2923, 2861, 1633, 1569 cm$^{-1}$ | ESI-HRMS (positive ion, sodium formate) calcd for C$_{18}$H$_{18}$N$_4$O ([M + H]$^+$) 319.1553; found 319.1552 | 11.6 | 97.0 |
| 40 | (4-methylphenyl-benzimidazole / pyrazole with Me, benzyl, OH) | NMR (DMSO-d6, δ): 2.17 (3H, s), 2.35 (3H, s), 3.60 (2H, s), 7.13-7.21 (1H, m), 7.23-7.31 (6H, m), 7.43 (1H, dd, J = 1.8, 8.2 Hz), 7.51-7.59 (3H, m), 7.72 (1H, br s) | IR (KBr): 3446, 3027, 2962, 2873, 1632, 1556 cm$^{-1}$ | ESI-HRMS (positive ion, sodium formate) calcd for C$_{25}$H$_{23}$N$_4$O ([M + H]$^+$) 395.1866; found 395.1852 | 13.6 | 98.0 |
| 41 | (4-methylphenyl-benzimidazole / pyrazole with Me, 4-chlorobenzyl, OH) | NMR (DMSO-d6, δ): 2.17 (3H, s), 2.34 (3H, s), 3.59 (2H, s), 7.24-7.36 (6H, m), 7.43 (1H, dd, J = 1.8 and 8.2 Hz), 7.52-7.59 (3H, m), 7.72 (1H, br s) | IR (KBr): 3253, 3028, 2921, 2894; 1655, 1557 cm$^{-1}$ | ESI-HRMS (negative ion, sodium formate) calcd for C$_{25}$H$_{20}$ClN$_4$O ([M + H]$^+$) 427.1331; found 427.1326 | 14.4 | 96.5 |
| 42 | (methyl-benzimidazole / pyrazole with Me, phenyl, OH) | NMR (DMSO-d6, δ): 2.39 (3H, s), 2.41 (3H, s), 7.07 (1H, dd, J = 0.9 and 8.2 Hz), 7.12-7.17 (1H, m), 7.32-7.38 (3H, m), 7.44 (1H, d, J = 8.2 Hz), 7.64-7.69 (2H, m) | IR (KBr): 3060, 1660, 1596, 1514 cm$^{-1}$ | ESI-HRMS (positive ion, sodium formate) calcd for C$_{18}$H$_{17}$N$_4$O ([M + H]$^+$) 305.1397; found 305.1402 | 11.8 | 98.6 |
| 43 | (methyl-benzimidazole / pyrazole with Me, diphenylmethyl, OH) | NMR (DMSO-d6, δ): 2.08 (3H, s), 5.28 (1H, s), 7.13-7.24 (4H, m), 7.26-7.33 (8H, m), 7.48-7.53 (2H, m) | IR (KBr): 3229, 3025, 1656, 1559 cm$^{-1}$ | ESI-HRMS (positive ion, sodium formate) calcd for C$_{24}$H$_{21}$N$_4$N ([M + H]$^+$) 381.1710; found 381.1707 | 13.0 | 98.0 |

TABLE 1-continued

| Ex. No. | 1H-NMR | IR | ESI-HRMS | HPLC retention time (min) | purity (%) |
|---|---|---|---|---|---|
| 44 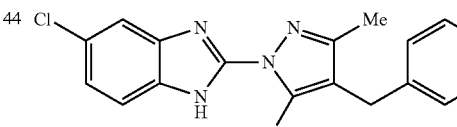 | NMR (DMSO-$d_6$, δ): 2.17 (3H, s), 3.59 (2H, s), 7.18 (1H, dd, J = 1.8 and 8.2 Hz), 7.28-7.35 (4H, m), 7.51 (1H, d, J = 8.2 Hz), 7.55 (1H, d, J = 1.8 Hz) | IR (KBr): 3294, 3077, 1630, 1568, 1536 cm$^{-1}$ | ESI-HRMS (positive ion, sodium formate) calcd for $C_{18}H_{15}Cl_2N_4O$ ([M + H]$^+$) 373.0617; found 373.0600 | 13.9 | 98.7 |
| 45 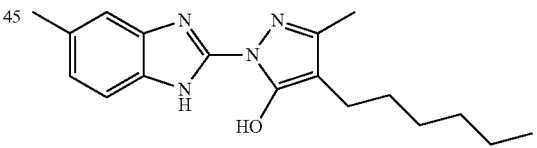 | NMR (DMSO-$d_6$, δ): 0.81-0.90 (3H, m), 1.21-1.34 (6H, m), 1.40-1.52 (2H, m), 2.16 (3H, s), 2.22 (2H, t, J = 7.3 Hz), 2.39 (3H, s), 6.97 (1H, dd, J = 0.9, 8.2 Hz), 7.31 (1H, br s), 7.39 (1H, d, J = 8.2 Hz) | IR (KBr): 3169, 3022, 2928, 2855, 1660, 1552 cm$^{-1}$ | ESI-HRMS (positive ion, sodium formate) calcd for $C_{18}H_{25}N_4O$ ([M + H]$^+$) 313.2022; found 313.2046 | 12.2 | 98.3 |
| 46 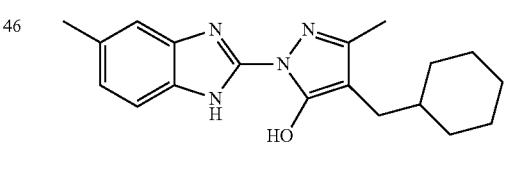 | NMR (DMSO-$d_6$, δ): 0.86-1.00 (2H, m), 1.08-1.24 (3H, m), 1.40-1.71 (6H, m), 2.11 (2H, d, J = 6.9 Hz), 2.15 (3H, s), 2.39 (3H, s), 6.97 (1H, dd, J = 0.9, 8.2 Hz), 7.31 (1H, br s), 7.38 (1H, d, J = 8.2 Hz) | IR (KBr): 3093, 2919, 2849, 2919, 1589, 1552 cm$^{-1}$ | ESI-HRMS (positive ion, sodium formate) calcd for $C_{18}H_{25}N_4O$ ([M + H]$^+$) 325.2823; found 325.2030 | 12.3 | 99.0 |
| 47 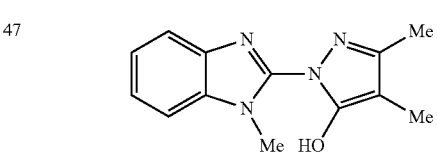 | NMR (CDCl$_3$, δ): 1.93 (3H, s), 2.22 (3H, s), 4.24 (3H, s), 7.28-7.36 (3H, m), 7.56-7.61 (1H, m) | IR (KBr): 3431, 3058, 2922, 2861, 1665, 1561, 1511 cm$^{-1}$ | ESI-HRMS (positive ion, sodium formate) calcd for $C_{13}H_{15}N_4O$ ([M + H]$^+$) 243.1240; found 243.1248 | 8.7 | 98.6 |
| 48 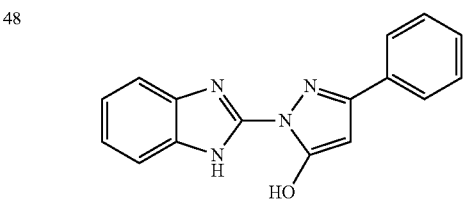 | NMR (DMSO-$d_6$, δ): 5.94 (1H, s), 7.22-7.28 (2H, m), 7.39-7.51 (3H, m), 7.55-7.61 (2H, m), 7.88-7.92 (2H, m) | IR (KBr): 3334, 3068, 1678; 1631, 1600, 1555 cm$^{-1}$ | ESI-HRMS (positive ion, sodium formate) calcd for $C_{16}H_{13}N_4O$ ([M + H]$^+$) 277.1084; found 277.1093 | 19.0 | 98.7 |

Furthermore, using the corresponding starting compounds and in the same manner as in Example 1, the compounds of Examples 49-57 were synthesized. The following Tables summarize the structures of Examples 49-57 and physico-chemical properties thereof.

TABLE 2

| Ex. No | 1H-NMR | IR | ESI-HRMS | HPLC retention time (min) | purity (%) |
|---|---|---|---|---|---|
| 49 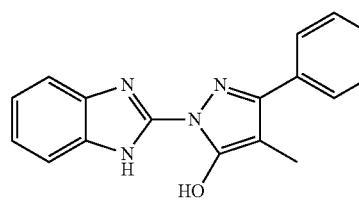 | NMR (DMSO-$d_6$, δ): 2.06 (3H, s), 7.18-7.24 (2H, m), 7.46-7.60 (5H, m), 7.73-7.78 (2H, m) | IR (KBr): 3173, 1665, 1640, 1662 cm$^{-1}$ | ESI-HRMS (positive ion, sodium formate) calcd for $C_{17}H_{15}N_4O$ ([M + H]$^+$) 291.1240; found 291.1236 | 11.1 | 98.1 |

TABLE 2-continued

| Ex. No | 1H-NMR | IR | ESI-HRMS | HPLC retention time (min) | purity (%) |
|---|---|---|---|---|---|
| 50 | NMR (DMSO-d$_6$, δ): 3.84 (2H, s), 7.13-7.29 (7H, m), 7.41-7.49 (3H, m), 7.55-7.66 (4H, m) | IR (KBr): 3186, 3061, 1665, 1633, 1591, 1559 cm$^{-1}$ | ESI-HRMS (positive ion, sodium formate) calcd for C$_{23}$H$_{19}$N$_4$O ([M + H]$^+$) 367.1663; found 367.1567 | 13.2 | 97.8 |
| 51 | NMR (DMSO-d$_6$, δ): 2.14 (3H, s), 2.38 (3H, s), 3.21 (2H, s), 6.98 (1H, d, J = 7.5 Hz), 7.31 (1H, s), 7.39 (1H, d, J = 7.5 Hz) | IR (KBr): 3175, 3034, 1679, 1651, 1635, 1605, 1559, 1507 cm$^{-1}$ | ESI-HRMS (negative ion, sodium formate) calcd for C$_{14}$H$_{13}$N$_4$O$_3$ ([M − H]$^-$) 285.0993; found 285.0983 | | |
| 52 | NMR (DMSO-d$_6$, δ): 7.14 (1H, t, J = 7.3 Hz), 7.20-7.30 (3H, m), 7.33 (2H, d, J =7.3 Hz), 7.37-7.45 (3H, m), 7.45-7.55 (2H, m), 7.58 (1H, d, J = 8.7 Hz), 7.62 (1H, br s) | IR (KBr): 3101, 3073, 3059, 1651, 1596, 1572, 1555, 1510, 1466 cm$^{-1}$ | ESI-HRMS (negative ion, sodium formate) calcd for C$_{22}$H$_{14}$ClN$_4$O ([M − H]$^-$) 385.0856; found 385.0870 | | |
| 53 | NMR (CDCl$_3$, δ): 2.00 (3H, s), 2.44 (3H, br s), 7.06 (1H, br s), 7.15-7.50 (7H, m), 8.43 (2H, br s) | IR (KBr): 3173, 3026, 2923, 1662, 1652, 1634, 1617, 1558, 1508, 1473 cm$^{-1}$ | ESI-HRMS (negative ion, sodium formate) calcd for C$_{18}$H$_{15}$N$_4$O ([M − H]$^-$) 303.1246; found 303.1269 | | |
| 54 | NMR (DMSO-d$_6$, δ): 2.17 (3H, s), 3.61 (2H, s), 7.13-7.22 (1H, m), 7.23-7.30 (4H, m), 7.32 (1H, dd, J = 8.2 and 1.8 Hz), 7.49 (1H, d, J = 8.2 Hz), 7.70 (1H, d, J = 1.8 Hz) | IR (KBr): 3030, 2923, 2850, 1706, 1637, 1592, 1576, 1545, 1509 cm$^{-1}$ | ESI-HRMS (negative ion, sodium formate) calcd for C$_{18}$H$_{14}$BrN$_4$O ([M − H]$^-$) 381.0345; found 381.0348 | | |
| 55 | NMR (CDCl$_3$, δ): 2.39 (3H, s), 7.04 (2H, d, J = 7.8 Hz), 7.05-7.50 (12H, m) | IR (KBr): 3419, 3059, 2974, 1641, 1615, 1600, 1565, 1513, 1469 cm$^{-1}$ | ESI-HRMS (negative ion, sodium formate) calcd for C$_{23}$H$_{17}$N$_4$O ([M − H]$^-$) 366.1402; found 365.1416 | | |
| 56 | NMR (CDCl$_3$, δ): 1.25 (3H, t, J = 7.3 Hz), 2.24 (3H, s), 2.44 (3H, s), 2.60-2.70 (4H, m), 4.12 (2H, q, J = 7.3 Hz), 7.05 (1H, d, J = 7.8 Hz), 7.23 (1H, s), 7.30 (1H, d, J = 7.8 Hz), | IR (KBr): 3206, 2978, 1732, 1654, 1559, 1489 cm$^{-1}$ | ESI-HRMS (negative ion, sodium formate) calcd for C$_{17}$H$_{19}$N$_4$O$_3$ ([M − H]$^-$) 327.1457; found 327.1349 | | |

TABLE 2-continued

| Ex. No | | 1H-NMR | IR | ESI-HRMS | HPLC retention time (min) | purity (%) |
|---|---|---|---|---|---|---|
| 57 | (structure: 5-methylbenzimidazole linked to N of pyrazole bearing 3-methyl, 5-OH, and 4-(CH2CH2COOH)) | NMR (DMSO-$d_6$, δ): 2.17 (3H, s), 2.36-2.55 (7H, m), 6.98 (1H, d, J = 7.8 Hz), 7.3 (1H, s), 7.39 (1H, d, J = 7.8 Hz) | IR (KBr): 3267, 2957, 1684, 1654, 1637, 1595, 1559, 1489 cm$^{-1}$ | ESI-HRMS (negative ion, sodium formate) calcd for $C_{15}H_{15}N_4O_3$ ([M − H]$^−$) 299.1139; found 299.1121 | | |

Experimental Example 1

Method for Evaluation of PCA-1 Inhibitory Activity

To an enzyme reaction solution (50 mM trishydrochloric acid buffer (pH 8.0), 2 mM ascorbic acid, 100 μM oxoglutaric acid, 40 μM ferric sulfate) containing 80 fmol 3-methyl cytosine-containing oligo DNA as a substrate were added a test compound (10 μM, 1 μM) and 4 ng silkworm recombinant PCA-1, and the mixture was incubated at 37° C. for 1 hr. After completion of the reaction, the enzyme reaction solution was 20-fold diluted with water to quench the reaction. Using 2 μL thereof, real-time PCR (Bio-Rad iQ SYBR Green Supermix) was performed in a 20 μL reaction system. The analytical curve was formed using a dilution series of the non-methylated oligoDNA. The primers used were forward primer 24 bases and reverse primer 22 bases. Reaction conditions: 95° C., 10 seconds→40 cycles of 95° C., 5 seconds, 61° C., 30 seconds, and 72° C., 15 seconds→95° C., 1 min→55° C., 1 min→55° C., 10 seconds, after which increased by 0.5° C. to 95° C. for 10 seconds→preserved at 25° C.

The degree of demethylation in the presence or absence of the test compound was compared and the inhibitory activity was evaluated.

The PCA-1 inhibitory activity of the compound of the present invention is shown in Table 3.

TABLE 3

| Example No. | PCA-1 inhibitory activity (%) | |
|---|---|---|
| | 10 μM | 1 μM |
| 1 | 81 | 24 |
| 3 | 60 | 21 |
| 4 | 82 | 50 |
| 5 | 91 | 50 |
| 11 | 82 | 36 |
| 13 | 76 | 19 |
| 14 | 80 | 35 |
| 15 | 76 | −1 |
| 17 | 76 | 25 |
| 18 | 74 | 27 |
| 19 | 76 | 38 |
| 24 | 67 | 61 |
| 25 | 68 | 39 |
| 31 | 85 | 47 |
| 32 | 81 | 49 |
| 33 | 82 | 54 |
| 34 | 80 | 49 |
| 35 | 77 | 25 |
| 37 | 64 | 38 |
| 40 | 61 | 21 |
| 42 | 65 | 37 |
| 43 | 73 | 50 |
| 45 | 81 | 43 |
| 46 | 81 | 47 |

Example Nos. 52-54, 56 and 57 also confirmed good PCA-1 inhibitory activity.

Experimental Example 2

Evaluation of Cancer Cell Proliferation Suppressive Action cell line used: DU145 (prostate cancer cell: Institute of Development, Aging and Cancer, Tohoku University, Cell Resource Center for Biomedical Research)
evaluation of scaffolding dependency growth suppressive action:

The cells were plated on a 96 well plate at 5×10$^3$ cells/well/ 90 μL, and cultured overnight. The test compound (10 μM) was added and, after culture for 48 hr, a 1:9 mixture of aqueous 1-methoxy-5-methylphenazinium methylsulfate (PMS) solution and 2-(4-iodophenyl)-3-(4-nitrophenyl)-5-(2,4-disulfophenyl)-2H-tetrazolium, monosodium salt (WST-1)/20 mM 4-(2-hydroxyethyl)-1-piperazineethanesulfonic acid (HEPES) solution (DOJIN) was added by 10 μL, and the absorbance was measured at 450 nm 2 hr later. As a control wavelength, 630 nm was used.

The cancer cell proliferation inhibitory activity of the compound of the present invention is shown in Table 4.

TABLE 4

| Example No. | DU145 proliferation inhibitory activity (%) |
|---|---|
| 1 | 60 |
| 13 | 22 |
| 14 | 45 |

Furthermore, the compound of the present invention also showed a cancer cell proliferation inhibitory activity against PC3 (other prostate cancer cell), and Mia-Paca2 and Panc-1 (pancreatic cancer cells).

Experimental Example 3

Evaluation of Antitumor Action Using Prostate Cancer Xenograft Model

A prostate cancer xenograft model was produced as shown below.

DU145 cells (4×10⁶ cells) were mixed with BD Matrigel Basememt Membrane Matrix High Concentration (Becton, Dickinson and Company), and subcutaneously transplanted to the back of BALB/c nu/nu mouse. After transplantation, the tumor was isolated when it reached a volume of about 200 mm³, and subcutaneously transplanted into the back of a different BALB/c nu/nu mouse. This operation was repeated three times to generate a tumor derived from DU145 cells that grow stably. A model mouse for the evaluation of the compound was prepared by finely cutting the in vivo passaged tumor into about 10 mm³, and subcutaneously transplanting same into the back of a BALB/c nu/nu mouse.

The compound of Example 1 was suspended in 0.5 w/v % sterile carboxycellulose (Wako Pure Chemical Industries, Ltd.), and subcutaneously administered to the back. The volume of the tumor was calculated using the formula of (long diameter)×(short diameter)²×0.5. The rate of changes in the tumor volume and body weight was evaluated and the results are shown in FIG. 1.

Industrial Applicability

The compound of the present invention has a superior action to inhibit the PCA-1 enzyme activity, and is useful for the prophylaxis and/or treatment of a disease involving PCA-1. Particularly, the compound of the present invention is useful as an anti-cancer agent against prostate cancer, pancreatic cancer, non-small cell lung cancer and the like.

This application is based on patent application No. 2012-045267 (filing date: Mar. 1, 2012) filed in Japan, the contents of which are encompassed in full herein.

The invention claimed is:

1. A compound represented by the formula (I):

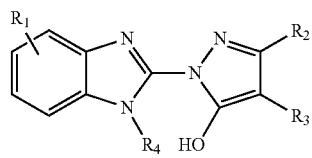

(I)

wherein
$R_1$ is
a $C_{1-6}$ alkyl group optionally substituted by a halogen atom,
a $C_{6-10}$ aryl group optionally substituted by one or more substituents selected from the group consisting of a halogen atom and a $C_{1-6}$ alkyl group, or
a halogen atom;
$R_2$ is a $C_{1-6}$ alkyl group or a $C_{6-10}$ aryl group;
$R_3$ is
a $C_{7-11}$ aralkyl group optionally substituted by one or more substituents selected from the group consisting of a halogen atom, a $C_{1-6}$ alkyl group optionally substituted by a halogen atom, a $C_{6-10}$ aryl group and a $C_{1-6}$ alkoxy group,
a $C_{6-10}$ aryl group, or
a $C_{1-6}$ alkyl group optionally substituted by one or more substituents selected from the group consisting of a $C_{6-10}$ aryl group, a $C_{1-6}$ alkoxy-carbonyl group, a carboxyl group, and a $C_{3-6}$ cycloalkyl group; and
$R_4$ is a hydrogen atom;
or a pharmaceutically acceptable salt thereof.

2. The compound according to claim 1 which is represented by the following formula:

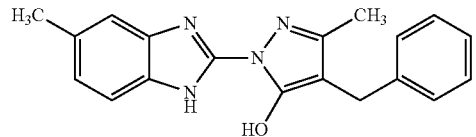 [SMILES: Cc1ccc2[nH]c(-n3nc(C)c(Cc4ccccc4)c3O)nc2c1]

or a pharmaceutically acceptable salt thereof.

3. A pharmaceutical composition comprising the compound according to claim 1 or a pharmaceutically acceptable salt thereof and a pharmaceutically acceptable carrier.

4. The pharmaceutical composition according to claim 3, wherein the compound is a compound represented by the following formula:

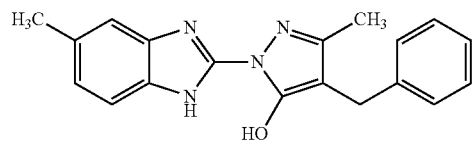 [SMILES: Cc1ccc2[nH]c(-n3nc(C)c(Cc4ccccc4)c3O)nc2c1]

or a pharmaceutically acceptable salt thereof.

* * * * *